US007364867B2

(12) United States Patent
Margolskee et al.

(10) Patent No.: US 7,364,867 B2
(45) Date of Patent: Apr. 29, 2008

(54) METHOD OF IDENTIFYING BITTER COMPOUNDS BY EMPLOYING TRP8, A TRANSIENT RECEPTOR POTENTIAL CHANNEL EXPRESSED IN TASTE RECEPTOR CELLS

(75) Inventors: Robert F. Margolskee, Upper Montclair, NJ (US); Liquan Huang, New Haven, CT (US); Minqing Rong, Brooklyn, NY (US); Marianna Max, West Orange, NJ (US); Cristian A. Perez, New York, NY (US)

(73) Assignee: The Mount Sinai School of Medicine, New York, NY (US)

( * ) Notice: Subject to any disclaimer, the term of this patent is extended or adjusted under 35 U.S.C. 154(b) by 216 days.

(21) Appl. No.: 09/834,792

(22) Filed: Apr. 13, 2001

(65) Prior Publication Data

US 2002/0037515 A1   Mar. 28, 2002

Related U.S. Application Data

(60) Provisional application No. 60/197,491, filed on Apr. 17, 2000.

(51) Int. Cl.
G01N 33/566 (2006.01)
(52) U.S. Cl. .................. 435/7.21; 435/7.1; 435/7.2
(58) Field of Classification Search .............. 530/300, 530/350; 435/7.1, 6
See application file for complete search history.

(56) References Cited

U.S. PATENT DOCUMENTS

| | | | |
|---|---|---|---|
| 4,376,110 A | 3/1983 | David et al. | |
| 4,826,824 A | 5/1989 | Schiffman | |
| 4,873,191 A | 10/1989 | Wagner et al. | |
| 4,946,778 A | 8/1990 | Ladner et al. | |
| 5,585,089 A | 12/1996 | Queen et al. | |
| 5,693,756 A | 12/1997 | Li et al. | |
| 6,558,910 B2 | 5/2003 | Zuker et al. | |
| 6,608,176 B2 | 8/2003 | Chaudhari et al. | |
| 2002/0115205 A1 | 8/2002 | Foord et al. | |
| 2002/0128433 A1 | 9/2002 | Yao et al. | |
| 2002/0143131 A1 | 10/2002 | Yao et al. | |
| 2002/0164645 A1* | 11/2002 | Zuker et al. ................. 435/7.1 |
| 2002/0168635 A1 | 11/2002 | Zuker et al. | |
| 2003/0045472 A1 | 3/2003 | Axel et al. | |
| 2003/0157568 A1 | 8/2003 | Zuker et al. | |
| 2003/0216545 A1 | 11/2003 | Spyteck et al. | |

| | | |
|---|---|---|
| 2004/0259160 A1 | 12/2004 | Johnson et al. |

FOREIGN PATENT DOCUMENTS

| | | |
|---|---|---|
| DE | 199 53 167 A1 | 7/2001 |
| WO | WO 97/04666 A1 | 2/1997 |
| WO | WO 00/40969 | 7/2000 |
| WO | WO 00/44929 A2 | 8/2000 |
| WO | WO 01/32693 A2 | 5/2001 |
| WO | WO 01/79448 A2 | 10/2001 |
| WO | WO 01/98526 A2 | 12/2001 |
| WO | WO 02/10382 A2 | 2/2002 |
| WO | WO 02/36622 A2 | 5/2002 |
| WO | WO 02/054069 A1 | 7/2002 |
| WO | WO 00/45179 A2 | 8/2002 |
| WO | WO 02/087306 A2 | 11/2002 |
| WO | WO 2004/076632 A2 | 9/2004 |

OTHER PUBLICATIONS

Estacion et al., Biochemical Journal, (Jul. 1, 1999) 341 ( Pt 1) 41-49.*
Okada et al., Journal of Biological Chemistry, (Sep. 24, 1999) 274 (39) 27359-70.*
Marshall "Gene Therapy's Growing Pains". Science, vol. 269 (1995), pp. 1050-1055.*
Orkin et al. "Report and recommendations of the panel to assess the NIH investment in research on gene therapy", (1995). pp. 1-39.*
Verma, I. M., et al. "Gene therapy-promise, problems, and prospects", Nature, vol. 389 (Sep. 1997), pp. 239-242.*
Chandrashekar-J et al., Nature 444(288-294)2006.*
Perez-CA et al., Nature Neuroscience 5(11)1169-1176, 2002.*
Liu and Liman, PNAS 100(15160-15165)2003.*
Prawitt-D et al., PNAS 100(25)15166-15171, 2003.*
Hofmann et al., Current Biology, 13(1153-1158)2003.*
Zhang-Z et al. J. Neuroscience 27(5777-5786)2007.*

(Continued)

*Primary Examiner*—John Ulm
(74) *Attorney, Agent, or Firm*—Nixon Peabody LLP

(57) ABSTRACT

The present invention relates to the discovery, identification and characterization of a transient receptor potential channel, referred to herein as TRP8, which is expressed in taste receptor cells and associated with the perception of bitter and sweet taste. The invention encompasses TRP8 nucleotides, host cell expression systems, TRP8 proteins, fusion proteins, polypeptides and peptides, antibodies to the TRP8 protein, transgenic animals that express a TRP8 transgene, and recombinant "knock-out" animals that do not express TRP8. The invention further relates to methods for identifying modulators of the TRP8-mediated taste response and the use of such modulators to either inhibit or promote the perception of bitterness or sweetness. The modulators of TRP8 activity may be used as flavor enhancers in foods, beverages and pharmaceuticals.

4 Claims, 18 Drawing Sheets

OTHER PUBLICATIONS

Figure 6B:
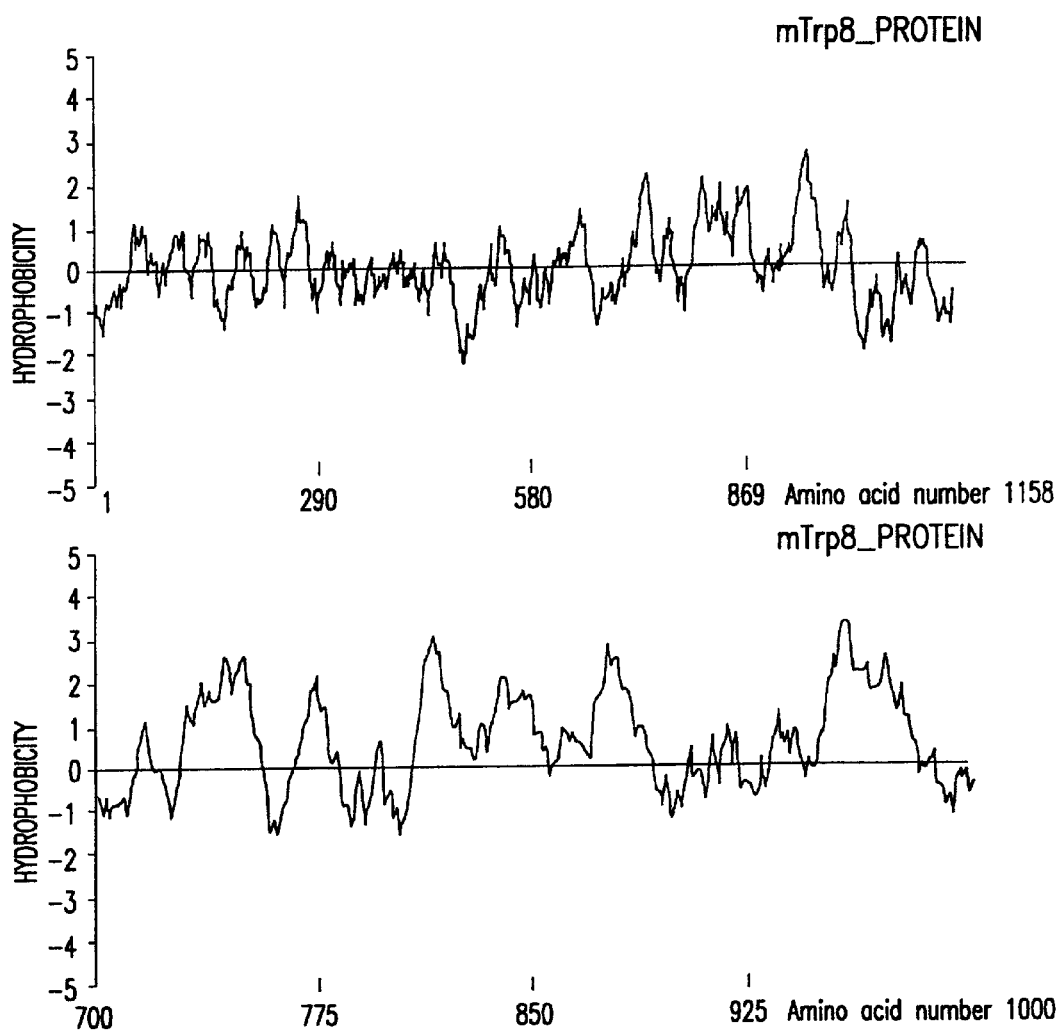

Akabas et al., "A Bitter Substance Induces a Rise in Intercellular Calcium in a Subpopulation of Rat Taste Cells," *Science* 242:1047-1050 (1988).

Asano-Miyoshi et al., "Co-Expression of Calcium Signaling Components in Vertebrate Taste Bud Cells," *Neurosci. Lett.* 283:61-64 (2000).

Ausubel et al., "Current Protocols in Molecular Biology," vol. 2, Green Publishing Associates, Inc. and John Wiley and Sons, Inc., New York, pp. 2.10.2-2.10.3 (1989).

Baxter et al., "A Novel Membrane Potential-Sensitive Fluorescent Dye Improves Cell-Based Assays for Ion Channels," *J. Biomol. Screen.* 7(1):79-85 (2002).

Behrendt et al., "Characterization of the Mouse Cold-Menthol Receptor TRPM8 and Vanilloid Receptor Type-1 VR1 Using a Fluorometric Imaging Plate Reader (FLIPR) Assay," *Brit. J. Pharmacol.* 141(4):737-745 (2004).

Bernhardt et al., "Changes in $IP_3$ and Cytosolic $Ca^{2+}$ in Response to Sugars and Non-Sugar Sweeteners in Transduction of Sweet Taste in the Rat," *J. Physiol.* 490.2:325-336 (1996).

Bird et al., "Single-Chain Antigen-Binding Proteins," *Science* 242(4877):423-426 (1988).

Bobanovic et al., "Molecular Cloning and Immunolocalization of a Novel Vertebrate *trp* Homologue from *Xenopus*," *Biochem. J.* 340:593-599 (1999).

Bronstein et al., "Chemiluminescent Reporter Gene Assays: Sensitive Detection of the GUS and SEAP Gene Products," *Biotechniques* 17(1):172-177 (1994).

Chomczynski & Sacchi, "Single-Step Method of RNA Isolation by Acid Guanidinium Thiocyanate-Phenol-Chloroform Extraction," *Anal. Biochem.* 162:156-159 (1987).

Cole et al., "The EBV-Hybridoma Technique and Its Application to Human Lung Cancer," in *Monoclonal Antibodies and Cancer Therapy*, Alan R. Liss, Inc., pp. 77-96 (1985).

Cote et al., "Generation of Human Monoclonal Antibodies Reactive with Cellular Antigens," *Proc. Natl. Acad. Sci. USA* 80:2026-2030 (1983).

Creighton, T.E., "Proteins: Structures and Molecular Principles," W.H. Freeman & Co., New York (1983) (Table of Contents Only).

Enklaar et al., "*Mtrl*, a Novel Biallelically Expressed Gene in the Center of the Mouse Distal Chromosome 7 Imprinting Cluster, is a Member of the *Trp* Gene Family," *Genomics* 67:179-187 (2000).

Falconer et al., "High-Throughput Screening for Ion Channel Modulators," *J. Biomol. Screen.* 7(5):460-465 (2002).

Filmore, D., "Cell-Based Screening Assays and Structural Studies are Fueling G-Protein Coupled Receptors as One of the Most Popular Classes of Investigational Drug Targets," *Modern Drug Discovery* pp. 24-26, 28 (2004).

Fleig et al., "Emerging Roles of TRPM Channels," in "Mammalian TRP Channels as Molecular Targets," *Novartis Foundation Symposium 258*, John Wiley & Sons, Ltd. pp. 248-266 (2004).

GenBank Accession No. AC003693 (Sep. 30, 1998).

GenBank Accession No. AF177473 (Jan. 20, 2000).

Gilbertson et al., "The Molecular Physiology of Taste Transduction," *Curr. Opin. Neurobiol.* 10:519-527 (2000).

Gill et al., "Flux Assays in High Throughput Screening of Ion Channels in Drug Discovery," *Assay and Drug Dev. Tech.* 1(5):709-717 (2003).

Gordon, J.W., "Transgenic Animals," *Intl. Rev. Cytol.* 115:171-229 (1989).

Herness, M.S., "Cellular Mechanisms of Taste Transduction," *Ann. Rev. Physiol.* 61:873-900 (1999).

Hofmann et al., "TRPM5 is a Voltage-Modulated and $Ca^{2+}$-Activated Monovalent Selective Cation Channel," *Current Biol.* 13:1153-1158 (2003).

Hoon et al., "Putative Mammalian Taste Receptors: A Class of Taste-Specific GPCRs with Distinct Topographic Selectivity," *Cell* 96:541-551 (1999).

Houghten et al., "Generation and Use of Synthetic Peptide Combinatorial Libraries for Basic Research and Drug Discovery," *Nature* 354:84-86 (1991).

Huang et al., "Gγ13 Colocalizes with Gustducin in Taste Receptor Cells and Mediates $IP_3$ Responses to Bitter Denatonium," *Nat. Neurosci.* 2(12):1055-1062 (1999).

Huston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85:5879-5883 (1988).

Kinnamon & Margolskee, "Mechanisms of Taste Transduction," *Curr. Opin. Neurobiol.* 6(4):506-513 (1996).

Köhler & Milstein, "Continuous Cultures of Fused Cells Secreting Antibody of Predefined Specificity," *Nature* 256:495-497 (1975).

Komuro & Rakic, "In Vitro Analysis of Signal Mechanisms Involved in Neuronal Migration," in L. W. Haynes ed., *The Neuron in Tissue Culture*, New York: John Wiley & Sons, pp. 57-69 (1999).

Kozbor & Roder, "The Production of Monoclonal Antibodies from Human Lymphocytes," *Immunology Today* 4(3):72-79 (1983).

Lakso et al., "Targeted Oncogene Activation by Site-Specific Recombination in Transgenic Mice," *Proc. Natl. Acad. Sci. USA* 89:6232-6236 (1992).

Lam et al., "A New Type of Synthetic Peptide Library for Identifying Ligand-Binding Activity," *Nature* 354:82-84 (1991).

Lavitrano et al., "Sperm Cells as Vectors for Introducing Foreign DNA into Eggs: Genetic Transformation of Mice," *Cell* 57:717-723 (1989).

Lindemann, B., "Receptors and Transduction in Taste," *Nature* 413:219-225 (2001).

Lindemann, B., "Taste Reception," *Physiological Reviews* 76(3):719-766 (1996).

Liu & Liman, "Intracellular $Ca^{2+}$ and the Phospholipid $PIP_2$ Regulate the Taste Transduction Ion Channel TRPM5," *PNAS* 100(25):15160-15165 (2003).

Lo, C.W., "Transformation by Iontophoretic Microinjection of DNA: Multiple Integrations Without Tandem Insertions," *Mol. Cell Biol.* 3(10):1803-1814 (1983).

McLaughlin et al., "Gustducin is a Taste-Cell-Specific G Protein Closely Related to the Transducins," *Nature* 357:563-569 (1992).

Ming et al., "Blocking Taste Receptor Activation of Gustducin Inhibits Gustatory Responses to Bitter Compounds," *Proc. Natl. Acad. Sci. USA* 96:9903-9908 (1999).

Ming et al., "Characterization and Solubilization of Bitter-Responsive Receptors That Couple to Gustducin," *Proc. Natl. Acad. Sci USA*, 95:8933-8938 (1998).

Montell, C., "New Light on TRP and TRPL," *Mol. Pharmacol.* 52:755-763 (1997).

Morrison et al., "Chimeric Human Antibody Molecules: Mouse Antigen-Binding Domains with Human Constant Region Domains," *Proc. Natl. Acad. Sci. USA* 81:6851-6855 (1984).

Neuberger et al., "Recombinant Antibodies Prossessing Novel Effector Functions," *Nature* 312:604-608 (1984).

Ninomiya et al., "Lack of Gurmarin Sensitivity of Sweet Taste Receptors Innervated by the Glossopharyngeal Nerve in C57BL Mice," *Am. J. Physiol.* 272(3 Pt 2):R1002-1006 (1997).

Perez et al., "A Transient Receptor Potential Channel Expressed in Taste Receptor Cells," *Nature Neurosci.* 5(11):1169-1176 (2002).

Prawitt et al., "Identification and Characterization of *MTR1*, A Novel Gene With Homology to Melastatin (*MLSN1*) and the *trp* Gene Family Located in the BWS-WT2 Critical Region on Chromosome 11p15.5 and Showing Allele-Specific Expression," *Human Molecular Genetics*, 9(2):203-216 (2000).

Ruiz-Avila et al., "Coupling of Bitter Receptor to Phosphodiesterase Through Transducin in Taste Receptor Cells," *Nature* 376:80-85 (1995).

Sambrook et al., "Molecular Cloning," 2nd Ed. Cold Spring Harbor Laboratory Press (1989) (Table of Contents only).

Songyang et al., "SH2 Domains Recognize Specific Phosphopeptide Sequences," *Cell* 72:767-788 (1993).

Takeda et al., "Construction of Chimaeric Processed Immunoglobulin Genes Containing Mouse Variable and Human Constant Region Sequences," *Nature* 314:452-454 (1985).

Thompson et al., "Germ Line Transmission and Expression of a Corrected HPRT Gene Produced by Gene Targeting in Embryonic Stem Cells," *Cell* 56:313-321 (1989).

van der Putten et al., "Efficient Insertion of Genes Into the Mouse Germ Line Via Retroviral Vectors," *Proc. Natl. Acad. Sci. USA* 82:6148-6152 (1985).

Ward et al., "Binding Activities of a Repertoire of Single Immunoglobulin Variable Domains Secreted from *Escherichia coli*," *Nature* 341:544-546 (1989).

Wolff et al., "Comparative Study of Membrane Potential-Sensitive Fluorescent Probes and Their Use in Ion Channel Screening Assays," *J. Biomol. Screening* 8(5):533-543.

Xu et al., "Ion-Channel Assay Technologies: *quo vadis?,*" *Drug Discov. Today* 6(24):1278-1287 (2001).

Alberts et al., Essential Cell Biology 372-373, 376-377 (1997).

Adler et al., "A Novel Family of Mammalian Taste Receptors," *Cell* 100:693-702 (2000).

Altenhofen et al., "Control of Ligand Specificity in Cyclic Nucleotide-gated Channels from Rod Photoreceptors and Olfactory Epithelium," *Proc. Nat'l Acad. Sci. USA* 88(21):9868-9872 (1991).

Bai et al., "Dimerization of the Extracellular Calcium-sensing Receptor (CaR) on the Cell Surface of CaR-transfected HEK293 Cells," *J. Biol. Chem.* 273(36):23605-23610 (1998).

Burnashev et al., "Fractional Calcium Currents Through Recombinant GluR Channels of the NMDA, AMPA and Kainate Receptor Subtypes," *J. Physiol.* 485(2):403-418 (1995).

Chandrashekar et al., "T2Rs Function as Bitter Taste Receptors," *Cell* 100(6):703-711 (2000).

Chaudhari et al., "A Metabotropic Glutamate Receptor Variant Functions as a Taste Receptor," *Nat. Neurosci.* 3(2):113-119 (2000).

Chaudhari & Roper, "Molecular and Physiological Evidence for Glutamate (*Umami*) Taste Transduction via a G Protein-coupled Receptor," *Ann. N.Y. Acad. Sci.* 855:398-406 (1998).

Chaudhari et al., "The Taste of Monosodium Glutamate: Membrane Receptors in Taste Buds," *J. Neurosci* 16(12):3817-3826 (1996).

Dhallan et al., "Primary Structure and Functional Expression of a Cyclic Nucleotide-activated Channel from Olfactory Neurons," *Nature* 247(6289):184-187 (1990).

Genbank Accession No. AA577486 (Sep. 12, 1997).

Genbank Accession No. AAF98120 (Aug. 9, 2000).

Genbank Accession No. AB039952 (Mar. 25, 2006).

Gilbertson, "Gustatory Mechanisms for the Detection of Fat," *Curr. Opin. Neurobiol.* 8(4):447-452 (1998).

Gillo et al., "Coexpression of *Drosophila* TRP and TRP-like Proteins in *Xenopus* Oocytes Reconstitutes Capacitative $Ca^{2+}$ Entry," *Proc. Natl. Acad. Sci. USA* 93:14146-14151 (1996).

Hu et al., "Appearance of a Novel $Ca^{2+}$ Influx Pathway in Sf9 Insect Cells Following Expression of the Transient Receptor Potential-like (*trpl*) Protein of *Drosophila*," *Biochem. Biophys. Res. Commun.* 201(2):1050-1056 (1994).

Kinnamon & Roper, "Passive and Active Membrane Properties of Mudpuppy Taste Receptor Cells," *J. Physiol.* 383:601-614 (1987).

Komuro & Rakic, "Orchestration of Neuronal Migration by Activity of Ion Channels, Neurotransmitter Receptors, and Intracelluar $Ca^{2+}$ Fluctuations," *J. Neurobiol.* 37(1):110-130 (1998).

Matsunami et al., "A Family of Candidate Taste Receptors in Human and Mouse," *Nature* 404:601-604 (2000).

Misaka et al., "Taste Buds Have a Cyclic Nucleotide-activated Channel, CNGgust," *J. Biol. Chem.* 272(36):22623-22629 (1997).

Naim et al., "Some Taste Substances Are Direct Activators of G-proteins," *Biochem. J.* 297:451-454 (1994).

Ogura et al., "Bitter Taste Transduction of Denatonium in the Mudpuppy *Necturus maculosus*," *J. Neurosci.* 17(10):3580-3587 (1997).

Principles of Neural Science 253-279 (Eric R. Kandel et al. eds., 4th ed. 2000).

Roper & McBride, "Distribution of Ion Channels on Taste Cells and Its Relationship to Chemosensory Transduction," *J. Membr. Biol.* 109(1):29-39 (1989).

Rössler et al., "Identification of a Phospholipase C β Subtype in Rat Taste Cells," *Eur. J. Cell Biol.* 77:253-261 (1998).

Thomas et al., "Identification of Synaptophysin as a Hexameric Channel Protein of the Synaptic Vesicle Membrane," *Science* 242(4881):1050-1053 (1988).

Weishaar et al., "A New Generation of Phosphodiesterase Inhibitors: Multiple Molecular Forms of Phosphodiesterase and the Potential for Drug Selectivity," *J. Med. Chem.* 28(5):538-545 (1985).

Wong et al., "Transduction of Bitter and Sweet Taste by Gustducin," *Nature* 381:796-800 (1996).

Zhang et al., "Increased Inwardly Rectifying Potassium Currents in HEK-293 Cells Expressing Murine Transient Receptor Potential 4," *Biochem. J.* 354(Pt 3):717-725 (2001).

* cited by examiner

```
cagctacatg ccattaatct ggaaggaacg ggcaggaaag ccaccatgca aacaacccag
agctcctgcc ccggcagccc cccagatact gaggatggct gggagcccat cctatgcagg
ggagagatca acttcggagg gtctgggaag aagcgaggca agtttgtgaa ggtgccaagc
agtgtggccc cctctgtgct ttttgaactc ctgctcaccg agtggcacct gccagccccc
aacctggtgg tgtccctggt gggtgaggaa cgacctttgg ctatgaagtc gtggcttcgg
gatgtcctgc gcaaggggct ggtgaaagca gctcagagca caggtgcctg gatcctgacc
agtgccctcc acgtgggcct ggcccgccat gttggacaag ctgtacgtga tcactctctg
gctagcacat ccaccaagat ccgtgtagtg gccatcggaa tggcctctct ggatcgaatc
cttcaccgtc aacttctaga tggtgtccac caaaaggagg atactcccat ccactaccca
gcagatgagg gcaacattca gggacccctc tgcccnctgg acagcaatct ctcccacttc
atccttgtgg agtcaggcgc ccttgggagt gggaacgacg ggctgacaga gctgcagctg
agcctggaga agcacatctc tcagcagagg acaggttatg ggggcaccag ctgcatccag
atacctgtcc tttgcctgtt ggtcaatggt gaccccaaca ccctagagag gatttccagg
gcagtggagc aggctgcccc atggctgatc ctggcaggtt ctggtggcat tgctgatgta
ctcgctgccc tggtgagcca gcctcatctc ctggtgcccc aggtggctga aagcagttc
agagagaaat tccccagcga gtgtttctct tgggaagcca ttgtacactg gacagagctg
ttacagaaca ttgctgcaca ccccacctg ctcacagtat atgacttcga gcaggagggt
tcggaggacc tggacactgt catcctcaag gcacttgtga aagcctgcaa gagccacagc
caagaagccc aagactacct agatgagctc aagttagcag tggcctggga tcgcgtggac
attgccaaga gtgaaatctt caatggggac gtggaatgga agtcctgtga cttggaagag
gtgatgacag atgccctcgt gagcaacaag cctgactttg tccgcctctt tgtggacagc
ggtgctgaca tggccgagtt cttgacctat gggcggctgc agcagcttta ccattctgtg
tcccccaaga gcctcctctt tgaactgctg cagcgtaagc atgaggaggg taggctgaca
ctggccggcc tgggtgccca gcaggctcgg gagctgccca ttggtctgcc tgccttctca
ctccacgagg tctcccgcgt actcaaagac ttcctgcatg acgcctgccg tggcttctac
caggacgggc gcaggatgga ggagagaggg ccacctaagc ggcccgcagg ccagaagtgg
ctgccagacc tcagtaggaa gagtgaagac ccttggaggg acctgttcct ctgggctgtg
ctgcagaatc gttatgagat ggccacatac ttctgggcca tgggccggga gggtgtggct
gctgctctgg ctgcctgcaa gatcataaag gaaatgtccc acctggagaa agaggcagag
gtggcccgca ccatgcgtga ggccaagtat gagcagctgg ccctggatct tttctcagag
tgctacggca acagtgagga ccgtgccttt gccctgctgg tgcgaggaa ccacagctgg
agcaggacca cgtgcctgca cctggccact gaagctgatg ccaaggcctt ctttgcccat
gacggtgtgc aagcattcct gaccaagatc tggtggggag acatggccac aggcacaccc
atcctacggc ttctgggtgc cttcacctgc ccagccctca tctacacaaa cctcatctcc
ttcagtgagg atgccccgca gaggatggac ctagaagatc tgcaggagcc agacagcttg
gatatggaaa agagcttcct atgcagccgg ggtggccaat ggagaagct aacagaggca
ccaagggctc caggcgatct aggcccacaa gctgccttcc tgctcacacg gtggaggaag
ttctggggcg ctcctgtgac tgtgttcctg gggaatgtgg tcatgtactt cgcattcctc
ttcctgttca cctatgtcct gctggtggac ttcaggccac caccccaggg gccgtctgga
tccgaggtta ccctctatt ctgggtgttc acactggtgc tggaggaaat ccgacagggc
ttcttcacag atgaggacac gcacctggtg aagaaattca ctctgtatgt ggaagacaac
tggaacaagt gtgacatggt ggccatcttc ctgttcattg tgggagtcac ctgtagaatg
gtgccctcgg tgtttgaggc tggcaggacc gttctggcca ttgacttcat ggtgttcaca
cttcggctca tccacatctt tgctattcac aagcagttgg gtcctaagat catcattgta
gagcgaatga tgaaggatgt cttcttttc ctcttcttcc tgagcgtatg gcttgtggcc
tatggtgtga ccactcaggc cctgctgcat ccccatgatg gccgtttgga gtggattttc
cgccgtgtgc tatacaggcc ttacctgcag atctttgggc aaatccctct ggatgaaatt
gatgaggctc gtgtgaactg ttctcttcac cctctgctgc tggaaagctc ggcttcctgc
cctaatctct atgccaactg gctggtcatt ctcctgctgg ttaccttcct gcttgtcact
```

FIG.1A (SEQ ID NO: 1)

```
aatgtgctgc tcatgaacct tctgatcgcc atgttcagct acacattcca ggtggtgcaa
ggcaatgcag acatgttctg gaagtttcaa cgctaccacc tcatcgttga ataccatgga
agaccagctc tggccccgcc cttcatcctg ctcagccacc tgagcctggt gctcaagcag
gtcttcagga aggaagccca gcataagcga caacatctgg agagagactt gcctgacccc
ttggaccaga agatcattac ctgggaaacg gttcaaaagg agaacttcct gagtaccatg
gagaaacgga ggagggacag cgaggggggag gtgctgagga aaacggcaca cagagtggac
ttgattgcca aatacatcgg ggggctgaga gagcaagaaa agaggatcaa gtgtctggaa
tcacaggcca actactgtat gctcctcttg tcctctatga cggatacact ggctccagga
ggcacctact caagctctca gaactgtggt tgcaggagtc agccagcctc tgctagagac
agggagtacc tagagtctgg cttgccaccc tctgacacct gaaatggaga aaccacttgc
tctagagccc cagacctggc cacatcgagt ttttggggca catcaacctt cccccactcc
cagcagcccc aagaaatggt cttcaaggcc ttgctacaga tcacttcttg gacatccctt
cctaagagaa tgaaactcat gtctttggca tctattcggg agcctcagaa gtatcctctc
cagcagggca agattttca tgtcccacta aagctttcac tggcttggac tggacagctg
gatctggcca agtcctacat aggacaccat ctgcctggat ggggctattt aggtctaacc
cctgtcttac cctgagttcc taagaagcca acctcttaaa cactaggttt ctttctgacc
cctgacccac tcattagctg accagctcct agagggcagg actcagatct attgtaatta
cctcccatct ttcaccccc acagcattat ctgtctgatc attctggcag aaaccccaag
atattgctca agggtaccca atgctacttt actttctata aagcctgtag accacctcaa
aaaaaaaaaa aaaaaaaaaa aaaaaaaaaa aaaaaaaaaa aaaaaaaaaa aaaaaaaaaa
aaaaaaaaaa aaaaaaa
```

FIG. 1B

MQTTQSSCPGSPPDTEDGWEPILCRGEINFGGSGKKRGKFVKVPSSVAPSVLFELLLTEWHLPAPNLVVSLVGEERPLAMKSWLRDVLR
KGLVKAAQSTGAWILTSALHVGLARHVGQAVRDHSLASTSTKIRVAIGMASLDRILHRQLLDGVHQKEDTPIHYPADEGNIQGPLCPL
DSNLSHFILVESGALGSGNDGLTELQLSLEKHISQQRTGYGGTSCIQIPVLCLLVNGDPNTLERISRAVEQAAPWLILAGSGGIADVLA
ALVSQPHLLVPQVAEKQFREKFPSECFSWEAIVHWTELLQNIAAHPHLLTVYDFEQEGSEDLDTVILKALVKACKSHSQEAQDYLDELK
LAVAWDRVDIAKSEIFNGDVEWKSCDLEEVMTDALVSNKPDFVRLFVDSGADMAEFLTYGRLQQLYHSVSPKSLLFELLQRKHEEGRLT
LAGLGAQQARELPIGLPAFSLHEVSRVLKDFLHDACRGFYQDGRRMEERGPPKRPAGQKWLPDLSRKSEDPWRDLFLWAVLQNRYEMAT
YFWAMGREGVAAALAACKIIKEMSHLEKEAEVARTMREAKYEQLALDLFSECYGNSEDRAFALLVRRNHSWSRTTCLHLATEADAKAFF
AHDGVQAFLTKIWWGDMATGTPILRLLGAFTCPALIYTNLISFSEDAPQRMDLEDLQEPDSLDMEKSFLCSRGGQLEKLTEAPRAPGDL
GPQAAFLLTRWRKFWGAPVTVFLGNVVMYFAFLFLFTYVLLVDFRPPPQGPSGSEVTLYFWVFTLVLEEIRQGFFTDEDTHLVKKFTLY
VEDNWNKCDMVAIFLFIVGVTCRMVPSVFEAGRTVLAIDFMVFTLRLIHIFAIHKQLGPKIIIVERMMKDVFFLFFLSVWLVAYGVTT
QALLHPHDGRLEWIFRRVLYRPYLQIFGQIPLDEIDEARVNCSLHPLLESSASCPNLYANWLVILLVTFLLVTNVLMNLLIAMFSY
TFQVVQGNADMFWKFQRYHLIVEYHGRPALAPPFILLSHLSLVLKQVFRKEAQHKRQHLERDLPDLDQKIITWETVQKENFLSTMEKR
RRDSEGEVLRKTAHRVDLIAKYIGGLREQEKRIKCLESQANYCMLLLSSMTDTLAPGGTYSSSQNCGCRSQPASARDREYLESGLPPSD
T

FIG. 2
(SEQ ID NO: 2)

```
atgcaggatg tccaaggccc ccgtcccgga agccccgggg atgctgaaga ccggcgggag
ctgggcttgc acaggggcga ggtcaacttt ggagggtctg ggaagaagcg aggcaagttt
gtacgggtgc cgagcggagt ggccccgtct gtgctctttg acctgctgct tgctgagtgg
cacctgccgg cccccaacct ggtggtgtcc ctggtgggtg aggagcagcc tttcgccatg
aagtcctggc tgcgggatgt gctgcgcaag gggctggtga aggcggctca gagcacagga
gcctggatcc tgaccagtgc cctccgcgtg ggcctggcca ggcatgtcgg gcaggccgtg
cgcgaccact cgctggccag cacgtccacc aaggtccgtg tggttgctgt cggcatggcc
tcgctgggcc gcgtcctgca ccgccgcatt ctggcggcgg cccaggagga ttttcctgtc
cactaccctg aggatgacgg cggcagccag ggccccctct gttcactgga cagcaacctc
tcccacttca tcctggtgga gccaggcccc ccggggaagg gcgatgggct gacggagctg
cggctgaggc tggagaagca catctcggag cagagggcgg gctacggggg cactggcagc
atcgagatcc ctgtcctctg cttgctggtc aatggtgatc ccaacacctt ggagaggatc
tccagggccg tggagcaggc tgccccgtgg ctgatcctgg taggctcggg gggcatcgcc
gatgtgcttg ctgccctagt gaaccagccc cacctcctgg tgcccaaggt ggccgagaag
cagtttaagg agaagttccc cagcaagcat ttctcttggg aggacatcgt gcgctggacc
aagctgctgc agaacatcac ctcacaccag cacctgctca ccgtgtatga cttcgagcag
gagggctccg aggagctgga cacggtcatc ctgaaggcgc tggtgaaagc ctgcaagagc
cacagccagg agcctcagga ctatctggat gagctcaagc tggccgtggc ctgggaccgc
gtggacatcg ccaagagtga gatcttcaat ggggacgtgg agtggaagtc ctgtgacctg
gaggaggtga tggtggacga cctggtcagc aacaagcccg agtttgtgcg cctctttgtg
gacaacggcg cagacgtggc cgacttcctg acgtatgggc ggctgcagga gctctaccgc
tccgtgtcac gcaagagcct gctcttcgac ctgctgcagc ggaagcagga ggaggcccgg
ctgacgctgg ccggcctggg cacccagcag gcccgggagc accccgcggg gccaccggcc
ttctccctgc acgaggtctc ccgcgtactc aaggacttcc tgcaggacgc ctgccgaggc
ttctaccagg acggccggcc aggggaccga aggagggcgg agaagggccc ggccaagcgg
cccacgggcc agaagtggct gctggacctg aaccagaaga gcgagaaccc ctggcgggac
ctgttcctgt gggccgtgct gcagaaccgc cacgagatgg ccacctactt ctgggccatg
ggccaggaag gtgtggcagc cgcactggcc gcctgcaaaa tcctcaaaga gatgtcgcac
ctggagacgg aggccgaggc ggcccgagcc acgcgcgagg cgaaatacga gcggctggcc
cttgacctct tctccgagtg ctacagcaac agtgaggccc gcgccttcgc cctgctggtg
cgccggaacc gctgctggag caagaccacc tgcctgcacc tggccaccga ggctgacgcc
aaggccttct ttgcccacga cggcgttcag gccttcctga ccaggatctg gtgggggac
atggccgcag gcacgcccat cctgcggctg ctaggagcct tcctctgccc cgccctcgtc
tataccaacc tcatcacctt cagtgaggaa gctcccctga ggacaggcct ggaggacctg
caggacctgg acagcctgga cacggagaag agcccgctgt atggcctgca gagccgggtg
gaggagctgg tggaggcgcc gagggctcag ggtgaccgag cccacgtgc tgtcttcctg
ctcacacgct ggcggaaatt ctggggcgct cccgtgactg tgttcctggg aacgtggtc
atgtacttcg ccttcctctt cctgttcacc tacgtcctgc tggtggactt caggccgccc
ccccagggcc cctcagggcc cgaggtcacc ctctacttct gggtctttac gctggtgctg
gaggaaatcc ggcagggctt cttcacagac gaggacacac acctggtgaa gaagttcaca
ctgtatgtgg gggacaactg gaacaagtgt gacatggtgg ccatcttcct gttcatcgth
gttgtcacct gcaggatgct gccgtcggcg tttgaggctg ccgcacggt cctcgccatg
gacttcatgg tgttcacgct gcggctgatc catatctttg ccatacacaa gcagctgggc
cccaagatca tcgtggtaga gcgcatgatg aaggacgtct tcttcttcct cttctttctg
agcgtgtggc tcgtggccta cggtgtcacc acccaggcgc tgctgcaccc ccatgacggc
cgcctggagt ggatcttccg ccgggtgctc taccggccct acctgcagat cttcggccag
atcccactgg acgagattga tgaagcccgt gtgaactgct ccacccaccc actgctgctg
gaggactcac catcctgccc cagcctctat gccaactggc tggtcatcct cctgctggtc
accttcctgt tggtcaccaa tgtgctgctc atgaacctgc tcatcgccat gttcagctac
acgttccagg tggtgcaggg caacgcagac atgttctgga gttccagcg ctacaaccctg
```

FIG. 3A (SEQ ID NO: 3)

```
attgtggagt accacgagcg ccccgccctg gccccgccct tcatcctgct cagccacctg
agcctgacgc tccgccgggt cttcaagaag gaggctgagc acaagcggga gcacctggag
agagacctgc cagacccct ggaccagaag gtcgtcacct gggagacagt ccagaaggag
aacttcctga gcaagatgga gaagcggagg agggacagcg aggggggaggt gctgcggaaa
accgcccaca gagtggactt cattgccaag tacctcgggg ggctgagaga gcaagaaaag
cgcatcaagt gtctggagtc acagatcaac tactgctcgg tgctcgtgtc ctccgtggct
gacgtgctgg cccagggtgg cggcccccgg agctctcagc actgtggcga gggaagccag
ctggtggctg ctgaccacag aggtggttta gatggctggg aacaacccgg ggctggccag
cctccctcgg acacatga
```

FIG.3B

```
MQDVQGPRPG SPGDAEDRRE LGLHRGEVNF GGSGKKRGKF VRVPSGVAPS
VLFDLLLAEW HLPAPNLVVS LVGEEQPFAM KSWLRDVLRK GLVKAAQSTG
AWILTSALRV GLARHVGQAV RDHSLASTST KVRVVAVGMA SLGRVLHRRI
LEEAQEDFPV HYPEDDGGSQ GPLCSLDSNL SHFILVEPGP PGKGDGLTEL
RLRLEKHISE QRAGYGGTGS IEIPVLCLLV NGDPNTLERI SRAVEQAAPW
LILVGSGGIA DVLAALVNQP HLLVPKVAEK QFKEKFPSKH FSWEDIVRWT
KLLQNITSHQ HLLTVYDFEQ EGSEELDTVI LKALVKACKS HSQEPQDYLD
ELKLAVAWDR VDIAKSEIFN GDVEWKSCDL EEVMVDALVS NKPEFVRLFV
DNGADVADFL TYGRLQELYR SVSRKSLLFD LLQRKQEEAR LTLAGLGTQQ
AREPPAGPPA FSLHEVSRVL KDFLQDACRG FYQDGRPGDR RRAEKGPAKR
PTGQKWLLDL NQKSENPWRD LFLWAVLQNR HEMATYFWAM GQEGVAAALA
ACKILKEMSH LETEAEAARA TREAKYERLA LDLFSECYSN SEARAFALLV
RRNRCWSKTT CLHLATEADA KAFFAHDGVQ AFLTRIWWGD MAAGTPILRL
LGAFLCPALV YTNLITFSEE APLRTGLEDL QDLDSLDTEK SPLYGLQSRV
EELVEAPRAQ GDRGPRAVFL LTRWRKFWGA PVTVFLGNVV MYFAFLFLFT
YVLLVDFRPP PQGPSGPEVT LYFWVFTLVL EEIRQGFFTD EDTHLVKKFT
LYVGDNWNKC DMVAIFLFIV GVTCRMLPSA FEAGRTVLAM DFMVFTLRLI
HIFAIHKQLG PKIIVVERMM KDVFFFLFFL SVWLVAYGVT TQALLHPHDG
RLEWIFRRVL YRPYLQIFGQ IPLDEIDEAR VNCSTHPLLL EDSPSCPSLY
ANWLVILLLV TFLLVTNVLL MNLLIAMFSY TFQVVQGNAD MFWKFQRYNL
IVEYHERPAL APPFILLSHL SLTLRRVFKK EAEHKREHLE RDLPDPLDQK
VVTWETVQKE NFLSKMEKRR RDSEGEVLRK TAHRVDFIAK YLGGLREQEK
RIKCLESQIN YCSVLVSSVA DVLAQGGGPR SSQHCGEGSQ LVAADHRGGL
DGWEQPGAGQ PPSDT*
```

FIG.4

(SEQ ID NO: 4)

```
mTrp8   MQTTQSSCPGSPPDTEDGWEPILCRGEINFGGSGKKRGKFVKVPSSVAPSVLFELLLTEW 60
hTRP8   MQDVQGPRPGSPGDAEDRRELGLHRGEVNFGGSGKKRGKFVRVPSGVAPSVLFDLLLAEW 60
        **  *   **** *:**    *  *  ***:*************:***.*******:***:**

mTrp8   HLPAPNLVVSLVGEERPLAMKSWLRDVLRKGLVKAAQSTGAWILTSALHVGLARHVGQAV 120
hTRP8   HLPAPNLVVSLVGEEQPFAMKSWLRDVLRKGLVKAAQSTGAWILTSALRVGLARHVGQAV 120
        ***************.*:***********************************:******* mTrp8   RDHSLASTSTKIRVVAIGMASLDRILHRQLLDGVHQKEDTPIHYPADEGNIQGPLCPLDS 180
hTRP8   RDHSLASTSTKVRVVAVGMASLGRVLHRRILEEAQ--EDFPVHYPEDDGSQGPLCSLDS 178
        *********::*.:***::*:   ** *:*** *:*   ***.* mTrp8   NLSHFILVESGALGSGNDGLTELQLSLEKHISQQRTGYGGTSCIQIPVLCLLVNGDPNTL 240
hTRP8   NLSHFILVEPGPPKG-DGLTELRLRLEKHISEQRAGYGGTGSIEIPVLCLLVNGDPNTL 237
        *********.*.  * ******:* ****::*****..*::***************** mTrp8   ERISRAVEQAAPWLILAGSGGIADVLAALVSQPHLLVPQVAEKQFREKFPSECFSWEAIV 300
hTRP8   ERISRAVEQAAPWLILVGSGGIADVLAALVNQPHLLVPKVAEKQFKEKFPSKHFSWEDIV 297
        ****************.*************.******:******:*****: :**** **

mTrp8   HWTELLQNIAAHPHLLTVYDFEQEGSEDLDTVILKALVKACKSHSQEAQDYLDELKLAVA 360
hTRP8   RWTKLLQNITSHQHLLTVYDFEQEGSEELDTVILKALVKACKSHSQEPQDYLDELKLAVA 357
        ::***::*: * *********:********************.********* mTrp8   WDRVDIAKSEIFNGDVEWKSCDLEEVMTDALVSNKPDFVRLFVDSGADMAEFLTYGRLQQ 420
hTRP8   WDRVDIAKSEIFNGDVEWKSCDLEEVMVDALVSNKPEFVRLFVDNGADVADFLTYGRLQE 417
        **************************.********:*******.***:*:********:

mTrp8   LYHSVSPKSLLFELLQRKHEEGRLTLAGLGAQQARELPIGLPAFSLHEVSRVLKDFLHDA 480
hTRP8   LYRSVSRKSLLFDLLQRKQEEARLTLAGLGTQQAREPPAGPPAFSLHEVSRVLKDFLQDA 477
        **:***:*****:*****:**.********:****  *.* *******************:**

mTrp8   CRGFYQDGR----RMEERGPPKRPAGQKWLPDLSRKSEDPWRDLFLWAVLQNRYEMATYF 536
hTRP8   CRGFYQDGRPGDRRRAEKGPAKRPTGQKWLLDLNQKSENPWRDLFLWAVLQNRHEMATYF 537
        *********    * *::.*:**** .:*:******************:**** mTrp8   WAMGREGVAAALAACKIIKEMSHLEKEAEVARTMREAKYEQLALDLFSECYGNSEDRAFA 596
hTRP8   WAMGQEGVAAALAACKILKEMSHLETEAEAARATREAKYERLALDLFSECYSNSEARAFA 597
        ****:************:******* ***.** *******:**********.***:****
```

FIG. 5

(SEQ ID NO: 6)

Classification and Secondary Structure Prediction of Membrane Proteins http://azusa.proteome.bio.tuat.ac.jp/sosui/

| | | | | |
|---|---|---|---|---|
| Orientation of the N-terminus of | mTrp8: | IN | | |
| Number of transmembrane helices of | mTrp8: | 6 | | |
| Position of transmembrane helices of | mTrp8: | helix | begin | end |
| | | 1 | 732 | 754 |
| | | 2 | 769 | 792 |
| | | 3 | 807 | 829 |
| | | 4 | 839 | 863 |
| | | 5 | 870 | 893 |
| | | 6 | 955 | 977 |
| Orientation of the N-terminus of | hTrp8: | IN | | |
| Number of transmembrane helices of | hTrp8: | 6 | | |
| Position of transmembrane helices of | hTrp8: | helix | begin | end |
| | | 1 | 733 | 755 |
| | | 2 | 770 | 792 |
| | | 3 | 807 | 829 |
| | | 4 | 843 | 863 |
| | | 5 | 873 | 893 |
| | | 6 | 955 | 977 |

FIG.6A

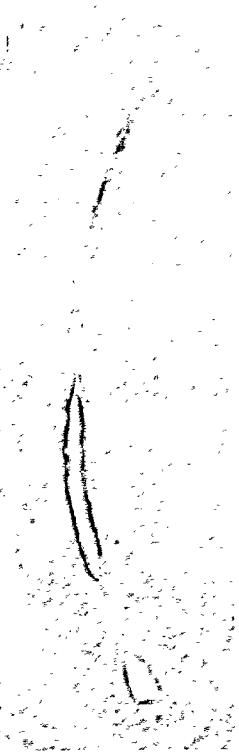
FIG.8A  FIG.8E  FIG.8B
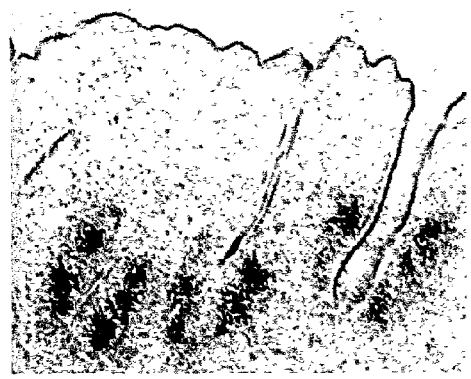
FIG.8C  FIG.8D

Figure 9G:

 
FIG.9AFIG.9B
 
FIG.9CFIG.9D
 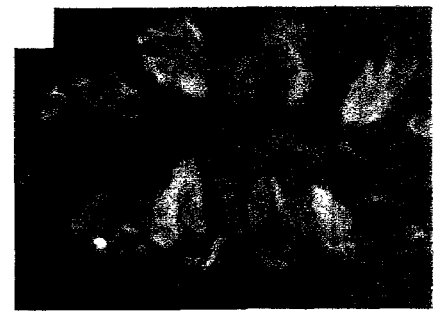
FIG.9EFIG.9F

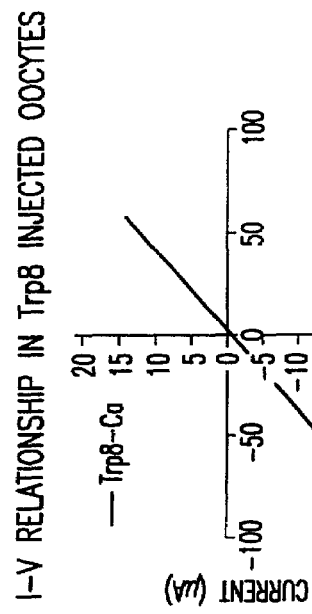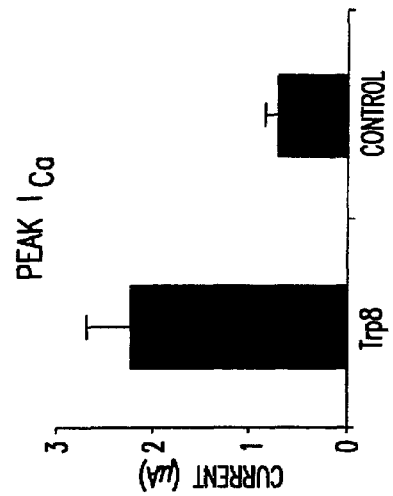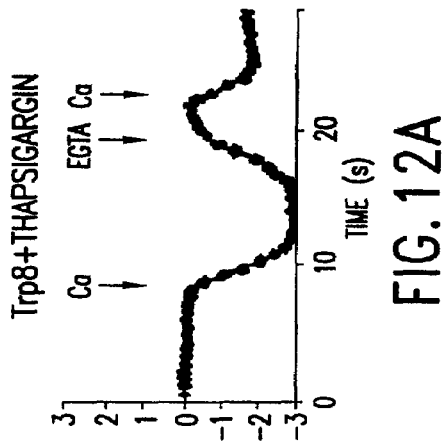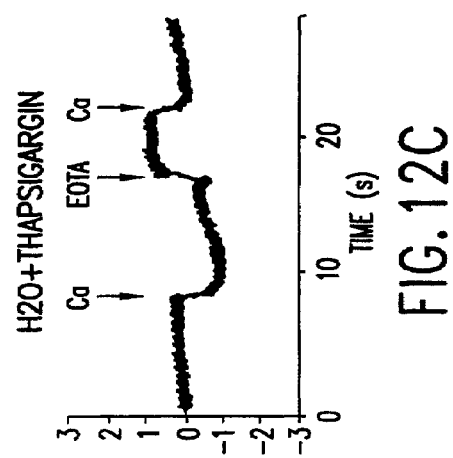

SEQUENCE LISTING

<160> NUMBER OF SEQ ID NOS: 4

<210> SEQ ID NO 1
<211> LENGTH: 4157
<212> TYPE: DNA
<213> ORGANISM: Murine TRP8 cDNA

<400> SEQUENCE: 1

```
cagctacatg ccattaatct ggaaggaacg ggcaggaaag ccaccatgca aacaacccag      60
agctcctgcc ccggcagccc cccagatact gaggatggct gggagcccat cctatgcagg     120
ggagagatca acttcggagg gtctgggaag aagcgaggca agtttgtgaa ggtgccaagc     180
agtgtggccc cctctgtgct ttttgaactc ctgctcaccg agtggcacct gccagccccc     240
aacctggtgg tgtccctggt gggtgaggaa cgacctttgg ctatgaagtc gtggcttcgg     300
gatgtcctgc gcaaggggct ggtgaaagca gctcagagca caggtgcctg gatcctgacc     360
agtgccctcc acgtgggcct ggcccgccat gttggacaag ctgtacgtga tcactctctg     420
gctagcacat ccaccaagat ccgtgtagtg gccatcggaa tggcctctct ggatcgaatc     480
cttcaccgtc aacttctaga tggtgtccac caaaaggagg atactcccat ccactaccca     540
gcagatgagg gcaacattca gggaccccotc tgcccoctgg acagcaatct ctcccacttc     600
atccttgtgg agtcaggcgc ccttgggagt gggaacgacg ggctgacaga gctgcagctg     660
agcctggaga agcacatctc tcagcagagg acaggttatg ggggcaccag ctgcatccag     720
atacctgtcc tttgcctgtt ggtcaatggt gacccaaca ccctagagag gatttccagg     780
gcagtggagc aggctgcccc atggctgatc ctggcaggtt ctggtggcat tgctgatgta     840
ctcgctgccc tggtgagcca gcctcatctc ctggtgcccc aggtggctga gaagcagttc     900
agagagaaat tccccagcga gtgtttctct tgggaagcca ttgtacactg gacagagctg     960
ttacagaaca ttgctgcaca cccccacctg ctcacagtat atgacttcga gcaggagggt    1020
tcggaggacc tggacactgt catcctcaag gcacttgtga aagcctgcaa gagccacagc    1080
caagaagccc aagactacct agatgagctc aagttagcag tggcctggga tcgcgtggac    1140
attgccaaga gtgaaatctt caatgggac gtggaatgga agtcctgtga cttggaagag    1200
gtgatgacag atgccctcgt gagcaacaag cctgactttg tccgcctctt tgtggacagc    1260
ggtgctgaca tggccgagtt cttgacctat gggcggctgc agcagcttta ccattctgtg    1320
tcccccaaga gcctcctctt tgaactgctg cagcgtaagc atgaggaggg taggctgaca    1380
```

-continued

```
ctggccggcc tgggtgccca gcaggctcgg gagctgccca ttggtctgcc tgccttctca      1440
ctccacgagg tctcccgcgt actcaaagac ttcctgcatg acgcctgccg tggcttctac      1500
caggacgggc gcaggatgga ggagagaggg ccacctaagc ggcccgcagg ccagaagtgg      1560
ctgccagacc tcagtaggaa gagtgaagac ccttggaggg acctgttcct ctgggctgtg      1620
ctgcagaatc gttatgagat ggccacatac ttctgggcca tgggccggga gggtgtggct      1680
gctgctctgg ctgcctgcaa gatcataaag gaaatgtccc acctggagaa agaggcagag      1740
gtggcccgca ccatgcgtga ggccaagtat gagcagctgg ccctggatct tttctcagag      1800
tgctacggca cagtgagga ccgtgccttt gccctgctgg tgcgaaggaa ccacagctgg      1860
agcaggacca cgtgcctgca cctggccact gaagctgatg ccaaggcctt ctttgcccat      1920
gacggtgtgc aagcattcct gaccaagatc tggtggggag acatggccac aggcacaccc      1980
atcctacggc ttctgggtgc cttcacctgc ccagccctca tctacacaaa cctcatctcc      2040
ttcagtgagg atgccccgca gaggatggac ctagaagatc tgcaggagcc agacagcttg      2100
gatatggaaa gagcttcct atgcagccgg ggtggccaat ggagaagct aacagaggca      2160 ccaagggctc caggcgatct aggcccacaa gctgccttcc tgctcacacg gtggaggaag      2220
ttctggggcg ctcctgtgac tgtgttcctg gggaatgtgg tcatgtactt cgcattcctc      2280
ttcctgttca cctatgtcct gctggtggac ttcaggccac caccccaggg gccgtctgga      2340
tccgaggtta ccctctattt ctgggtgttc acactggtgc tggaggaaat ccgacagggc      2400
ttcttcacag atgaggacac gcacctggtg aagaaattca ctctgtatgt ggaagacaac      2460
tggaacaagt gtgacatggt ggccatcttc ctgttcattg tgggagtcac ctgtagaatg      2520
gtgccctcgg tgtttgaggc tgcaggacc gttctggcca ttgacttcat ggtgttcaca      2580
cttcggctca tccacatctt tgctattcac aagcagttgg gtcctaagat catcattgta      2640
gagcgaatga tgaaggatgt cttctttttc ctcttcttcc tgagcgtatg gcttgtggcc      2700
tatggtgtga ccactcaggc cctgctgcat ccccatgatg gccgtttgga gtggattttc      2760
cgccgtgtgc tatacaggcc ttacctgcag atctttgggc aaatccctct ggatgaaatt      2820
gatgaggctc gtgtgaactg ttctcttcac cctctgctgc tggaaagctc ggcttcctgc      2880
cctaatctct atgccaactg gctggtcatt ctcctgctgg ttaccttcct gcttgtcact      2940
aatgtgctgc tcatgaacct tctgatcgcc atgttcagct acacattcca ggtggtgcaa      3000
ggcaatgcag acatgttctg gaagtttcaa cgctaccacc tcatcgttga ataccatgga      3060
agaccagctc tggcccgcc cttcatcctg ctcagccacc tgagcctggt gctcaagcag      3120
gtcttcagga aggaagccca gcataagcga caacatctgg agagagactt gcctgacccc      3180
ttggaccaga agatcattac ctgggaaacg gttcaaaagg agaacttcct gagtaccatg      3240
gagaaacgga ggagggacag cgagggggag gtgctgagga aaacggcaca cagagtggac      3300
ttgattgcca aatacatcgg ggggctgaga gagcaagaaa agaggatcaa gtgtctggaa      3360
tcacaggcca actactgtat gctcctcttg tcctctatga cggatacact ggctccagga      3420
ggcacctact caagctctca gaactgtggt tgcaggagtc agccagcctc tgctagagac      3480
agggagtacc tagagtctgg cttgccaccc tctgacacct gaaatggaga aaccacttgc      3540
tctagagccc cagacctggc cacatcgagt ttttggggca catcaacctt cccccactcc      3600
cagcagcccc aagaaatggt cttcaaggcc ttgctacaga tcacttcttg gacatccctt      3660
cctaagagaa tgaaactcat gtctttggca tctattcggg agcctcagaa gtatcctctc      3720
cagcagggca agattttca tgtcccacta aagctttcac tggcttggac tggacagctg      3780
```

-continued

```
gatctggcca agtcctacat aggacaccat ctgcctggat ggggctattt aggtctaacc    3840
cctgtcttac cctgagttcc taagaagcca acctcttaaa cactaggttt ctttctgacc    3900
cctgacccac tcattagctg accagctcct agagggcagg actcagatct attgtaatta    3960
cctcccatct ttcaccccc acagcattat ctgtctgatc attctggcag aaaccccaag    4020
atattgctca agggtaccca atgctacttt actttctata aagcctgtag accacctcaa    4080
aaaaaaaaaa aaaaaaaaaa aaaaaaaaaa aaaaaaaaaa aaaaaaaaaa aaaaaaaaaa    4140
aaaaaaaaaa aaaaaa                                                    4157
```

<210> SEQ ID NO 2
<211> LENGTH: 1158
<212> TYPE: PRT
<213> ORGANISM: Murine TRP8

<400> SEQUENCE: 2

```
Met Gln Thr Thr Gln Ser Ser Cys Pro Gly Ser Pro Asp Thr Glu
 1               5                  10                  15

Asp Gly Trp Glu Pro Ile Leu Cys Arg Gly Glu Ile Asn Phe Gly Gly
                20                  25                  30

Ser Gly Lys Lys Arg Gly Lys Phe Val Lys Val Pro Ser Ser Val Ala
            35                  40                  45

Pro Ser Val Leu Phe Glu Leu Leu Thr Glu Trp His Leu Pro Ala
 50                  55                  60

Pro Asn Leu Val Val Ser Leu Val Gly Glu Glu Arg Pro Leu Ala Met
 65                  70                  75                  80

Lys Ser Trp Leu Arg Asp Val Leu Arg Lys Gly Leu Val Lys Ala Ala
                85                  90                  95

Gln Ser Thr Gly Ala Trp Ile Leu Thr Ser Ala Leu His Val Gly Leu
            100                 105                 110

Ala Arg His Val Gly Gln Ala Val Arg Asp His Ser Leu Ala Ser Thr
        115                 120                 125

Ser Thr Lys Ile Arg Val Val Ala Ile Gly Met Ala Ser Leu Asp Arg
    130                 135                 140

Ile Leu His Arg Gln Leu Leu Asp Gly Val His Gln Lys Glu Asp Thr
145                 150                 155                 160

Pro Ile His Tyr Pro Ala Asp Glu Gly Asn Ile Gln Gly Pro Leu Cys
                165                 170                 175

Pro Leu Asp Ser Asn Leu Ser His Phe Ile Leu Val Glu Ser Gly Ala
            180                 185                 190

Leu Gly Ser Gly Asn Asp Gly Leu Thr Glu Leu Gln Leu Ser Leu Glu
        195                 200                 205

Lys His Ile Ser Gln Gln Arg Thr Gly Tyr Gly Gly Thr Ser Cys Ile
    210                 215                 220

Gln Ile Pro Val Leu Cys Leu Leu Val Asn Gly Asp Pro Asn Thr Leu
225                 230                 235                 240

Glu Arg Ile Ser Arg Ala Val Glu Gln Ala Ala Pro Trp Leu Ile Leu
                245                 250                 255

Ala Gly Ser Gly Gly Ile Ala Asp Val Leu Ala Ala Leu Val Ser Gln
            260                 265                 270

Pro His Leu Leu Val Pro Gln Val Ala Glu Lys Gln Phe Arg Glu Lys
        275                 280                 285

Phe Pro Ser Glu Cys Phe Ser Trp Glu Ala Ile Val His Trp Thr Glu
    290                 295                 300
```

```
Leu Leu Gln Asn Ile Ala Ala His Pro His Leu Leu Thr Val Tyr Asp
305                 310                 315                 320

Phe Glu Gln Glu Gly Ser Glu Asp Leu Asp Thr Val Ile Leu Lys Ala
            325                 330                 335

Leu Val Lys Ala Cys Lys Ser His Ser Gln Glu Ala Gln Asp Tyr Leu
                340                 345                 350

Asp Glu Leu Lys Leu Ala Val Ala Trp Asp Arg Val Asp Ile Ala Lys
            355                 360                 365

Ser Glu Ile Phe Asn Gly Asp Val Glu Trp Lys Ser Cys Asp Leu Glu
            370                 375                 380

Glu Val Met Thr Asp Ala Leu Val Ser Asn Lys Pro Asp Phe Val Arg
385                 390                 395                 400

Leu Phe Val Asp Ser Gly Ala Asp Met Ala Glu Phe Leu Thr Tyr Gly
                405                 410                 415

Arg Leu Gln Gln Leu Tyr His Ser Val Ser Pro Lys Ser Leu Leu Phe
            420                 425                 430

Glu Leu Leu Gln Arg Lys His Glu Glu Gly Arg Leu Thr Leu Ala Gly
            435                 440                 445

Leu Gly Ala Gln Gln Ala Arg Glu Leu Pro Ile Gly Leu Pro Ala Phe
450                 455                 460

Ser Leu His Glu Val Ser Arg Val Leu Lys Asp Phe Leu His Asp Ala
465                 470                 475                 480

Cys Arg Gly Phe Tyr Gln Asp Gly Arg Arg Met Glu Glu Arg Gly Pro
                485                 490                 495

Pro Lys Arg Pro Ala Gly Gln Lys Trp Leu Pro Asp Leu Ser Arg Lys
            500                 505                 510

Ser Glu Asp Pro Trp Arg Asp Leu Phe Leu Trp Ala Val Leu Gln Asn
            515                 520                 525

Arg Tyr Glu Met Ala Thr Tyr Phe Trp Ala Met Gly Arg Glu Gly Val
            530                 535                 540

Ala Ala Ala Leu Ala Ala Cys Lys Ile Ile Lys Glu Met Ser His Leu
545                 550                 555                 560

Glu Lys Glu Ala Glu Val Ala Arg Thr Met Arg Glu Ala Lys Tyr Glu
                565                 570                 575

Gln Leu Ala Leu Asp Leu Phe Ser Glu Cys Tyr Gly Asn Ser Glu Asp
            580                 585                 590

Arg Ala Phe Ala Leu Leu Val Arg Arg Asn His Ser Trp Ser Arg Thr
            595                 600                 605

Thr Cys Leu His Leu Ala Thr Glu Ala Asp Ala Lys Ala Phe Phe Ala
610                 615                 620

His Asp Gly Val Gln Ala Phe Leu Thr Lys Ile Trp Trp Gly Asp Met
625                 630                 635                 640

Ala Thr Gly Thr Pro Ile Leu Arg Leu Leu Gly Ala Phe Thr Cys Pro
                645                 650                 655

Ala Leu Ile Tyr Thr Asn Leu Ile Ser Phe Ser Glu Asp Ala Pro Gln
            660                 665                 670

Arg Met Asp Leu Glu Asp Leu Gln Glu Pro Asp Ser Leu Asp Met Glu
            675                 680                 685

Lys Ser Phe Leu Cys Ser Arg Gly Gly Gln Leu Glu Lys Leu Thr Glu
            690                 695                 700

Ala Pro Arg Ala Pro Gly Asp Leu Gly Pro Gln Ala Ala Phe Leu Leu
705                 710                 715                 720
```

-continued

Thr Arg Trp Arg Lys Phe Trp Gly Ala Pro Val Thr Val Phe Leu Gly
            725                 730                 735

Asn Val Val Met Tyr Phe Ala Phe Leu Phe Leu Phe Thr Tyr Val Leu
                740                 745                 750

Leu Val Asp Phe Arg Pro Pro Gln Gly Pro Ser Gly Ser Glu Val
            755                 760                 765

Thr Leu Tyr Phe Trp Val Phe Thr Leu Val Leu Glu Glu Ile Arg Gln
        770                 775                 780

Gly Phe Phe Thr Asp Glu Asp Thr His Leu Val Lys Lys Phe Thr Leu
785                 790                 795                 800

Tyr Val Glu Asp Asn Trp Asn Lys Cys Asp Met Val Ala Ile Phe Leu
                805                 810                 815

Phe Ile Val Gly Val Thr Cys Arg Met Val Pro Ser Val Phe Glu Ala
            820                 825                 830

Gly Arg Thr Val Leu Ala Ile Asp Phe Met Val Phe Thr Leu Arg Leu
        835                 840                 845

Ile His Ile Phe Ala Ile His Lys Gln Leu Gly Pro Lys Ile Ile Ile
        850                 855                 860

Val Glu Arg Met Met Lys Asp Val Phe Phe Leu Phe Phe Leu Ser
865                 870                 875                 880

Val Trp Leu Val Ala Tyr Gly Val Thr Thr Gln Ala Leu Leu His Pro
                885                 890                 895

His Asp Gly Arg Leu Glu Trp Ile Phe Arg Arg Val Leu Tyr Arg Pro
            900                 905                 910

Tyr Leu Gln Ile Phe Gly Gln Ile Pro Leu Asp Glu Ile Asp Glu Ala
        915                 920                 925

Arg Val Asn Cys Ser Leu His Pro Leu Leu Leu Glu Ser Ser Ala Ser
    930                 935                 940

Cys Pro Asn Leu Tyr Ala Asn Trp Leu Val Ile Leu Leu Leu Val Thr
945                 950                 955                 960

Phe Leu Leu Val Thr Asn Val Leu Leu Met Asn Leu Leu Ile Ala Met
                965                 970                 975

Phe Ser Tyr Thr Phe Gln Val Val Gln Gly Asn Ala Asp Met Phe Trp
            980                 985                 990

Lys Phe Gln Arg Tyr His Leu Ile Val Glu Tyr His Gly Arg Pro Ala
        995                 1000                1005

Leu Ala Pro Pro Phe Ile Leu Leu Ser His Leu Ser Leu Val Leu Lys
    1010                1015                1020

Gln Val Phe Arg Lys Glu Ala Gln His Lys Arg Gln His Leu Glu Arg
1025                1030                1035                1040

Asp Leu Pro Asp Pro Leu Asp Gln Lys Ile Ile Thr Trp Glu Thr Val
                1045                1050                1055

Gln Lys Glu Asn Phe Leu Ser Thr Met Glu Lys Arg Arg Arg Asp Ser
            1060                1065                1070

Glu Gly Glu Val Leu Arg Lys Thr Ala His Arg Val Asp Leu Ile Ala
        1075                1080                1085

Lys Tyr Ile Gly Gly Leu Arg Glu Gln Glu Lys Arg Ile Lys Cys Leu
        1090                1095                1100

Glu Ser Gln Ala Asn Tyr Cys Met Leu Leu Leu Ser Ser Met Thr Asp
1105                1110                1115                1120

Thr Leu Ala Pro Gly Gly Thr Tyr Ser Ser Gln Asn Cys Gly Cys
                1125                1130                1135

Arg Ser Gln Pro Ala Ser Ala Arg Asp Arg Glu Tyr Leu Glu Ser Gly

Leu Pro Pro Ser Asp Thr
     1155

<210> SEQ ID NO 3
<211> LENGTH: 3498
<212> TYPE: DNA
<213> ORGANISM: Human TRP8 CDNA

<400> SEQUENCE: 3

| | | | | | |
|---|---|---|---|---|---|
| atgcaggatg | tccaaggccc | ccgtcccgga | agccccgggg | atgctgaaga | ccggcgggag | 60 |
| ctgggcttgc | acaggggcga | ggtcaacttt | ggagggtctg | ggaagaagcg | aggcaagttt | 120 |
| gtacgggtgc | cgagcggagt | ggccccgtct | gtgctctttg | acctgctgct | tgctgagtgg | 180 |
| cacctgccgg | ccccccaacct | ggtggtgtcc | ctggtgggtg | aggagcagcc | tttcgccatg | 240 |
| aagtcctggc | tgcgggatgt | gctgcgcaag | gggctggtga | aggcggctca | gagcacagga | 300 |
| gcctggatcc | tgaccagtgc | cctccgcgtg | gcctggcca | ggcatgtcgg | gcaggccgtg | 360 |
| cgcgaccact | cgctggccag | cacgtccacc | aaggtccgtg | tggttgctgt | cggcatggcc | 420 |
| tcgctgggcc | gcgtcctgca | ccgccgcatt | ctggaggagg | cccaggagga | ttttcctgtc | 480 |
| cactaccctg | aggatgacgg | cggcagccag | ggcccctct | gttcactgga | cagcaacctc | 540 |
| tcccacttca | tcctggtgga | gccaggcccc | cggggaagg | gcgatgggct | gacggagctg | 600 |
| cggctgaggc | tggagaagca | catctcggag | cagagggcgg | gctacggggg | cactggcagc | 660 |
| atcgagatcc | ctgtcctctg | cttgctggtc | aatggtgatc | ccaacacctt | ggagaggatc | 720 |
| tccagggccg | tggagcaggc | tgccccgtgg | ctgatcctgg | taggctcggg | gggcatcgcc | 780 |
| gatgtgcttg | ctgccctagt | gaaccagccc | cacctcctgg | tgcccaaggt | ggccgagaag | 840 |
| cagtttaagg | agaagttccc | cagcaagcat | ttctcttggg | aggacatcgt | gcgctggacc | 900 |
| aagctgctgc | agaacatcac | ctcacaccag | cacctgctca | ccgtgtatga | cttcgagcag | 960 |
| gagggctccg | aggagctgga | cacggtcatc | ctgaaggcgc | tggtgaaagc | ctgcaagagc | 1020 |
| cacagccagg | agcctcagga | ctatctggat | gagctcaagc | tggccgtggc | ctgggaccgc | 1080 |
| gtggacatcg | ccaagagtga | gatcttcaat | ggggacgtgg | agtggaagtc | ctgtgacctg | 1140 |
| gaggaggtga | tggtggacgc | cctggtcagc | aacaagcccg | agtttgtgcg | cctcttttgt | 1200 |
| gacaacggcg | cagacgtggc | cgacttcctg | acgtatgggc | ggctgcagga | gctctaccgc | 1260 |
| tccgtgtcac | gcaagagcct | gctcttcgac | ctgctgcagc | ggaagcagga | ggaggcccgg | 1320 |
| ctgacgctgg | ccggcctggg | cacccagcag | gcccgggagc | cacccgcggg | gccaccggcc | 1380 |
| ttctcccctgc | acgaggtctc | ccgcgtactc | aaggacttcc | tgcaggacgc | ctgccgaggc | 1440 |
| ttctaccagg | acggccggcc | aggggaccgc | aggagggcgg | agaagggccc | ggccaagcgg | 1500 |
| cccacgggcc | agaagtggct | gctggacctg | aaccagaaga | gcgagaaccc | ctggcgggac | 1560 |
| ctgttcctgt | gggccgtgct | gcagaaccgc | cacgagatgg | ccacctactt | ctgggccatg | 1620 |
| ggccaggaag | gtgtggcagc | cgcactggcc | gcctgcaaaa | tcctcaaaga | gatgtcgcac | 1680 |
| ctggagacgg | aggccgaggc | ggcccgagcc | acgcgcgagg | cgaaatacga | gcggctggcc | 1740 |
| cttgacctct | ctccgagtg | ctacagcaac | agtgaggccc | cgcgccttcgc | cctgctggtg | 1800 |
| cgccggaacc | gctgctggag | caagaccacc | tgcctgcacc | tggccaccga | ggctgacgcc | 1860 |
| aaggccttct | tgcccacga | cggcgttcag | gccttcctga | ccaggatctg | gtgggggac | 1920 |
| atggccgcag | gcacgcccat | cctgcggctg | ctaggagcct | tcctctgccc | cgccctcgtc | 1980 |

```
tataccaacc tcatcacctt cagtgaggaa gctcccctga ggacaggcct ggaggacctg    2040
caggacctgg acagcctgga cacggagaag agcccgctgt atggcctgca gagccgggtg    2100
gaggagctgg tggaggcgcc gagggctcag ggtgaccgag gccacgtgc tgtcttcctg     2160 ctcacacgct ggcggaaatt ctggggcgct cccgtgactg tgttcctggg aacgtggtc    2220 atgtacttcg ccttcctctt cctgttcacc tacgtcctgc tggtggactt caggccgccc    2280
ccccagggcc cctcagggcc cgaggtcacc ctctacttct gggtctttac gctggtgctg    2340
gaggaaatcc ggcagggctt cttcacagac gaggacacac acctggtgaa gaagttcaca    2400
ctgtatgtgg ggacaactg gaacaagtgt gacatggtg ccatcttcct gttcatcgtg      2460
ggtgtcacct gcaggatgct gccgtcggcg tttgaggctg ccgcacggt cctcgccatg     2520 gacttcatgg tgttcacgct gcggctgatc catatctttg ccatacacaa gcagctgggc    2580
cccaagatca tcgtggtaga gcgcatgatg aaggacgtct tcttcttcct cttctttctg    2640
agcgtgtggc tcgtggccta cggtgtcacc acccaggcgc tgctgcaccc ccatgacggc    2700
cgcctggagt ggatcttccg ccgggtgctc taccggccct acctgcagat cttcggccag    2760
atcccactga cgagattga tgaagcccgt gtgaactgct ccacccaccc actgctgctg    2820
gaggactcac catcctgccc cagcctctat gccaactggc tggtcatcct cctgctggtc    2880
accttcctgt tggtcaccaa tgtgctgctc atgaacctgc tcatcgccat gttcagctac    2940
acgttccagg tggtgcaggg caacgcagac atgttctgga agttccagcg ctacaacctg    3000
attgtggagt accacgagcg ccccgccctg gccccgccct catcctgct cagccacctg     3060 agcctgacgc tccgccgggt cttcaagaag gaggctgagc acaagcggga gcacctggag    3120
agagacctgc cagaccccct ggaccagaag gtcgtcacct gggagacagt ccagaaggag    3180
aacttcctga gcaagatgga gaagcggagg agggacagcg aggggaggt gctgcggaaa    3240 accgcccaca gagtggactt cattgccaag tacctcgggg gctgagagag caagaaaag    3300 cgcatcaagt gtctggagtc acagatcaac tactgctcgg tgctcgtgtc ctccgtggct    3360
gacgtgctgg cccagggtgg cggccccgg agctctcagc actgtggcga gggaagccag    3420
ctggtggctg ctgaccacag aggtggttta gatggctggg aacaacccgg ggctggccag    3480
cctccctcgg acacatga                                                  3498
```

<210> SEQ ID NO 4
<211> LENGTH: 1165
<212> TYPE: PRT
<213> ORGANISM: Human

<400> SEQUENCE: 4

Met Gln Asp Val Gln Gly Pro Arg Pro Gly Ser Pro Gly Asp Ala Glu
1               5                   10                  15

Asp Arg Arg Glu Leu Gly Leu His Arg Gly Glu Val Asn Phe Gly Gly
            20                  25                  30

Ser Gly Lys Lys Arg Gly Lys Phe Val Arg Val Pro Ser Gly Val Ala
        35                  40                  45

Pro Ser Val Leu Phe Asp Leu Leu Ala Glu Trp His Leu Pro Ala
    50                  55                  60

Pro Asn Leu Val Val Ser Leu Val Gly Glu Gln Pro Phe Ala Met
65                  70                  75                  80

Lys Ser Trp Leu Arg Asp Val Leu Arg Lys Gly Leu Val Lys Ala Ala
                85                  90                  95

Gln Ser Thr Gly Ala Trp Ile Leu Thr Ser Ala Leu Arg Val Gly Leu

```
                100             105             110
Ala Arg His Val Gly Gln Ala Val Arg Asp His Ser Leu Ala Ser Thr
            115                 120                 125
Ser Thr Lys Val Arg Val Val Ala Val Gly Met Ala Ser Leu Gly Arg
    130                 135                 140
Val Leu His Arg Arg Ile Leu Glu Glu Ala Gln Glu Asp Phe Pro Val
145                 150                 155                 160
His Tyr Pro Glu Asp Gly Gly Ser Gln Gly Pro Leu Cys Ser Leu
                165                 170                 175
Asp Ser Asn Leu Ser His Phe Ile Leu Val Glu Pro Gly Pro Pro Gly
            180                 185                 190
Lys Gly Asp Gly Leu Thr Glu Leu Arg Leu Arg Leu Glu Lys His Ile
            195                 200                 205
Ser Glu Gln Arg Ala Gly Tyr Gly Gly Thr Gly Ser Ile Glu Ile Pro
            210                 215                 220
Val Leu Cys Leu Leu Val Asn Gly Asp Pro Asn Thr Leu Glu Arg Ile
225                 230                 235                 240
Ser Arg Ala Val Glu Gln Ala Ala Pro Trp Leu Ile Leu Val Gly Ser
            245                 250                 255
Gly Gly Ile Ala Asp Val Leu Ala Ala Leu Val Asn Gln Pro His Leu
            260                 265                 270
Leu Val Pro Lys Val Ala Glu Lys Gln Phe Lys Glu Lys Phe Pro Ser
        275                 280                 285
Lys His Phe Ser Trp Glu Asp Ile Val Arg Trp Thr Lys Leu Leu Gln
    290                 295                 300
Asn Ile Thr Ser His Gln His Leu Leu Thr Val Tyr Asp Phe Glu Gln
305                 310                 315                 320
Glu Gly Ser Glu Glu Leu Asp Thr Val Ile Leu Lys Ala Leu Val Lys
            325                 330                 335
Ala Cys Lys Ser His Ser Gln Glu Pro Gln Asp Tyr Leu Asp Glu Leu
            340                 345                 350
Lys Leu Ala Val Ala Trp Asp Arg Val Asp Ile Ala Lys Ser Glu Ile
        355                 360                 365
Phe Asn Gly Asp Val Glu Trp Lys Ser Cys Asp Leu Glu Glu Val Met
    370                 375                 380
Val Asp Ala Leu Val Ser Asn Lys Pro Glu Phe Val Arg Leu Phe Val
385                 390                 395                 400
Asp Asn Gly Ala Asp Val Ala Asp Phe Leu Thr Tyr Gly Arg Leu Gln
            405                 410                 415
Glu Leu Tyr Arg Ser Val Ser Arg Lys Ser Leu Leu Phe Asp Leu Leu
        420                 425                 430
Gln Arg Lys Gln Glu Glu Ala Arg Leu Thr Leu Ala Gly Leu Gly Thr
    435                 440                 445
Gln Gln Ala Arg Glu Pro Pro Ala Gly Pro Pro Ala Phe Ser Leu His
    450                 455                 460
Glu Val Ser Arg Val Leu Lys Asp Phe Leu Gln Asp Ala Cys Arg Gly
465                 470                 475                 480
Phe Tyr Gln Asp Gly Arg Pro Gly Asp Arg Arg Ala Glu Lys Gly
            485                 490                 495
Pro Ala Lys Arg Pro Thr Gly Gln Lys Trp Leu Leu Asp Leu Asn Gln
        500                 505                 510
Lys Ser Glu Asn Pro Trp Arg Asp Leu Phe Leu Trp Ala Val Leu Gln
    515                 520                 525
```

```
Asn Arg His Glu Met Ala Thr Tyr Phe Trp Ala Met Gly Gln Glu Gly
    530                 535                 540

Val Ala Ala Ala Leu Ala Ala Cys Lys Ile Leu Lys Glu Met Ser His
545                 550                 555                 560

Leu Glu Thr Glu Ala Glu Ala Arg Ala Thr Arg Glu Ala Lys Tyr
                    565                 570                 575

Glu Arg Leu Ala Leu Asp Leu Phe Ser Glu Cys Tyr Ser Asn Ser Glu
                580                 585                 590

Ala Arg Ala Phe Ala Leu Leu Val Arg Arg Asn Arg Cys Trp Ser Lys
            595                 600                 605

Thr Thr Cys Leu His Leu Ala Thr Glu Ala Asp Ala Lys Ala Phe Phe
        610                 615                 620

Ala His Asp Gly Val Gln Ala Phe Leu Thr Arg Ile Trp Trp Gly Asp
625                 630                 635                 640

Met Ala Ala Gly Thr Pro Ile Leu Arg Leu Gly Ala Phe Leu Cys
                    645                 650                 655

Pro Ala Leu Val Tyr Thr Asn Leu Ile Thr Phe Ser Glu Glu Ala Pro
                660                 665                 670

Leu Arg Thr Gly Leu Glu Asp Leu Gln Asp Leu Asp Ser Leu Asp Thr
            675                 680                 685

Glu Lys Ser Pro Leu Tyr Gly Leu Gln Ser Arg Val Glu Glu Leu Val
        690                 695                 700

Glu Ala Pro Arg Ala Gln Gly Asp Arg Gly Pro Arg Ala Val Phe Leu
705                 710                 715                 720

Leu Thr Arg Trp Arg Lys Phe Trp Gly Ala Pro Val Thr Val Phe Leu
                    725                 730                 735

Gly Asn Val Val Met Tyr Phe Ala Phe Leu Phe Leu Phe Thr Tyr Val
                740                 745                 750

Leu Leu Val Asp Phe Arg Pro Pro Gln Gly Pro Ser Gly Pro Glu
            755                 760                 765

Val Thr Leu Tyr Phe Trp Val Phe Thr Leu Val Leu Glu Glu Ile Arg
770                 775                 780

Gln Gly Phe Phe Thr Asp Glu Asp Thr His Leu Val Lys Lys Phe Thr
785                 790                 795                 800

Leu Tyr Val Gly Asp Asn Trp Asn Lys Cys Asp Met Val Ala Ile Phe
                805                 810                 815

Leu Phe Ile Val Gly Val Thr Cys Arg Met Leu Pro Ser Ala Phe Glu
            820                 825                 830

Ala Gly Arg Thr Val Leu Ala Met Asp Phe Met Val Phe Thr Leu Arg
        835                 840                 845

Leu Ile His Ile Phe Ala Ile His Lys Gln Leu Gly Pro Lys Ile Ile
    850                 855                 860

Val Val Glu Arg Met Met Lys Asp Val Phe Phe Phe Leu Phe Phe Leu
865                 870                 875                 880

Ser Val Trp Leu Val Ala Tyr Gly Val Thr Thr Gln Ala Leu Leu His
                    885                 890                 895

Pro His Asp Gly Arg Leu Glu Trp Ile Phe Arg Arg Val Leu Tyr Arg
                900                 905                 910

Pro Tyr Leu Gln Ile Phe Gly Gln Ile Pro Leu Asp Glu Ile Asp Glu
            915                 920                 925

Ala Arg Val Asn Cys Ser Thr His Pro Leu Leu Leu Glu Asp Ser Pro
        930                 935                 940
```

-continued

```
Ser Cys Pro Ser Leu Tyr Ala Asn Trp Leu Val Ile Leu Leu Leu Val
945                 950                 955                 960

Thr Phe Leu Leu Val Thr Asn Val Leu Leu Met Asn Leu Leu Ile Ala
                965                 970                 975

Met Phe Ser Tyr Thr Phe Gln Val Val Gln Gly Asn Ala Asp Met Phe
            980                 985                 990

Trp Lys Phe Gln Arg Tyr Asn Leu Ile Val Glu Tyr His Glu Arg Pro
        995                 1000                1005

Ala Leu Ala Pro Pro Phe Ile Leu Leu Ser His Leu Ser Leu Thr Leu
    1010                1015                1020

Arg Arg Val Phe Lys Lys Glu Ala Glu His Lys Arg Glu His Leu Glu
1025                1030                1035                1040

Arg Asp Leu Pro Asp Pro Leu Asp Gln Lys Val Val Thr Trp Glu Thr
                1045                1050                1055

Val Gln Lys Glu Asn Phe Leu Ser Lys Met Glu Lys Arg Arg Arg Asp
            1060                1065                1070

Ser Glu Gly Glu Val Leu Arg Lys Thr Ala His Arg Val Asp Phe Ile
        1075                1080                1085

Ala Lys Tyr Leu Gly Gly Leu Arg Glu Gln Glu Lys Arg Ile Lys Cys
    1090                1095                1100

Leu Glu Ser Gln Ile Asn Tyr Cys Ser Val Leu Val Ser Ser Val Ala
1105                1110                1115                1120

Asp Val Leu Ala Gln Gly Gly Gly Pro Arg Ser Ser Gln His Cys Gly
                1125                1130                1135

Glu Gly Ser Gln Leu Val Ala Ala Asp His Arg Gly Gly Leu Asp Gly
            1140                1145                1150

Trp Glu Gln Pro Gly Ala Gly Gln Pro Pro Ser Asp Thr
        1155                1160                1165
```

METHOD OF IDENTIFYING BITTER COMPOUNDS BY EMPLOYING TRP8, A TRANSIENT RECEPTOR POTENTIAL CHANNEL EXPRESSED IN TASTE RECEPTOR CELLS

This Application claims priority under 35 U.S.C 119(e) to U.S. application No. 60/197,491 filed Apr. 17, 2000.

1. INTRODUCTION

The present invention relates to the discovery, identification and characterization of a transient receptor potential channel, referred to herein as TRP8, which is expressed in taste receptor cells and associated with the perception of bitter and sweet taste. The invention encompasses TRP8 nucleotides, host cell expression systems, TRP8 proteins, fusion proteins, polypeptides and peptides, antibodies to the TRP8 protein, transgenic animals that express a TRP8 transgene, and recombinant "knock-out" animals that do not express TRP8. The invention further relates to methods for identifying modulators of the TRP8-mediated taste response and the use of such modulators to either inhibit or promote the perception of bitterness or sweetness. The modulators of TRP8 activity may be used as flavor enhancers in foods, beverages and pharmaceuticals.

2. BACKGROUND OF THE INVENTION

Mammals are generally thought to have five basic categories of taste perception: salt, sour, sweet, bitter and umami (monosodium glutamate) (for review, see Lindemann, 1996, *Physiological Reviews,* 76:719-766; Herness and Gilbertson, 1999, *Annu Rev. Physiol.*, 61:873:900). The taste signals are sensed by specialized taste receptor cells (TRCs), which are organized into taste buds. Each taste bud comprises between about 50 and 100 individual cells grouped into a cluster that is between 20 and 40 microns in diameter. Nerve fibers enter from the base of the taste bud and synapse onto some of the taste receptor cells. Typically, a single TRC contacts several sensory nerve fibers, and each sensory fiber innervates several TRCs in the same taste bud (Lindemann, supra).

TRCs of most, if not all, vertebrate species possess voltage-gated sodium, potassium, and calcium ion channels with properties similar to those of neurons (Kinnamon, S. C. & Margolskee, R. F., 1996, *Curr. Opin. Neurobiol.* 6:506-513). Different types of primary tastes appear to utilize different types of transduction mechanisms, and certain types of tastes may employ multiple mechanisms which may reflect varying nutritional requirements amongst species (Kinnamon & Margolskee, supra).

Bitter and sweet taste transduction are thought to involve cAMP and $IP_3$ (Kinnamon & Margolskee, supra). The bitter compound denatonium causes calcium ion release from rat TRCs and the rapid elevation of $IP_3$ levels in rodent taste tissue (Id., citing Bernhardt, S J. et al., 1996, *J. Physiol.* (London) 490:325-336 and Akabas, M. H., et al., 1988, *Science* 242:1047-1050). Since denatonium cannot pass the cell membrane, it has been suggested that it may activate G-protein-coupled receptors, whereby the α and/or βγ G protein subunits would activate phospholipase C, leading to $IP_3$ generation and the release of calcium ions (Kinnamon & Margolskee, supra).

In recent years, a taste-specific G protein termed "gustducin", which is homologous to the retinal G protein, transducin, has been cloned and characterized (Id., citing McLaughlin, S. et al., 1992, *Nature* (London) 357:563-569). It is believed that gustducin plays a direct role in both bitter and sweet transduction. For example, gustducin and subunit (α-gustducin) null (knockout) mice had a reduced aversion to bitter compounds. Unexpectedly, the mice also exhibited a preference for sweet compounds suggesting involvement of gustducin in sweet transduction.

Recent biochemical experiments have demonstrated that taste receptor preparations activate transducin and gustducin in response to denatonium and other bitter compounds (Ming et al., 1998, *Proc. Natl. Acad. Sci.* USA 95:8933-8).

To thoroughly understand the molecular mechanisms underlying taste sensation, it is important to identify each molecular component in the taste signal transduction pathways. The present invention relates to the cloning of an ion channel, TRP8 (transient receptor potential channel 8), that is believed to be involved in taste transduction and may be involved in the changes in intra-cellular calcium ions associated with bitter taste perception.

3. SUMMARY OF THE INVENTION

The present invention relates to the discovery, identification and characterization of a transient receptor potential (TRP) channel, referred to hereafter as TRP8, that participates in the taste signal transduction pathway. TRP8 is a channel protein with a high degree of structural similarity to the family of calcium channel proteins known as transient receptor potential channels. As demonstrated by Northern Blot analysis, expression of the TRP8 transcript is tightly regulated, with the highest level of gene expression found in taste tissue, moderate expression in stomach and small intestine, and very low level expression in uterus and testis. In situ hybridization indicated expression of TRP8 in circumvallate and foliate papillae, but not in the surrounding non-gustatory epithelia. Additionally, the general pattern of TRP8 expression was comparable to that of α-gustducin, although the α-gustducin signal was somewhat more intense.

The present invention encompasses TRP8 nucleotides, host cells expressing such nucleotides and the expression products of such nucleotides. The invention encompasses TRP8 protein, TRP8 fusion proteins, antibodies to the TRP8 channel protein and transgenic animals that express a TRP8 transgene or recombinant knock-out animals that do not express the TRP8 protein.

Further, the present invention also relates to screening methods that utilize the TRP8 gene and/or TRP8 gene products as targets for the identification of compounds which modulate, i.e., act as agonists or antagonists, of TRP8 activity and/or expression. Compounds which stimulate taste responses similar to those of bitter tastants can be used as additives to provoke a desired aversive response—for example to discourage ingestion of compositions containing these compounds by children or animals. Compounds which inhibit the activity of the TRP8 channel may be used to block the perception of bitterness. The inhibitors of TRP8 may be used as flavor enhancers in foods, beverages or pharmaceuticals by decreasing or eliminating the perception of bitter taste.

The invention is based, in part, on the discovery of a channel protein expressed at high levels in taste receptor cells. In taste transduction, bitter compounds are thought to act via the G-proteins, such as gustducin, which in turn regulate second messenger systems. Co-localization of α-gustducin, γ-gustducin, phospholipase $C\beta_2$ ($PLC\beta_2$) and TRP8 to one subset of taste receptor cells indicates that they may function in the same transduction pathway. It is believed that TRP8 responds to tastant induced inositol triphosphate (IP$_3$)/diacylglycerol (DAG) generation by flooding the taste cell with extracellular calcium and activating calcium dependent down stream messengers leading to transmitter release into the synapse and activation of afferent gustatory nerves.

3.1. DEFINITIONS

As used herein, italicizing the name of TRP8 shall indicate the TRP8 gene, in contrast to its encoded protein product which is indicated by the name of TRP8 in the absence of italicizing. For example, "TRP8" shall mean the TRP8 gene, whereas "TRP8" shall indicate the protein product of the TRP8 gene.

4. BRIEF DESCRIPTION OF THE DRAWINGS

FIGS. 1A-B. Nucleotide sequence of the murine TRP8 cDNA encoding murine TRP8, SEQ ID NO: 1.

FIG. 2. Deduced amino acid sequence of the murine TRP8 transient receptor potential channel, SEQ ID NO: 2.

FIGS. 3A-B. Nucleotide sequence of the human TRP8 cDNA encoding human TRP8, SEQ ID NO: 3.

FIG. 4. Deduced amino acid sequence of the human TRP8 protein transient receptor potential channel, SEQ ID NO: 4.

FIG. 5. Amino acid sequence of the murine TRP8 (upper lines);
    versus human TRP8 (lower lines), as represented in part by SEQ ID NO: 2 and SEQ ID NO: 4, respectively, and displayed in SEQ ID NO: 6. Each pair of lines corresponds to a predicted mouse/human exon.

Figure 6C:
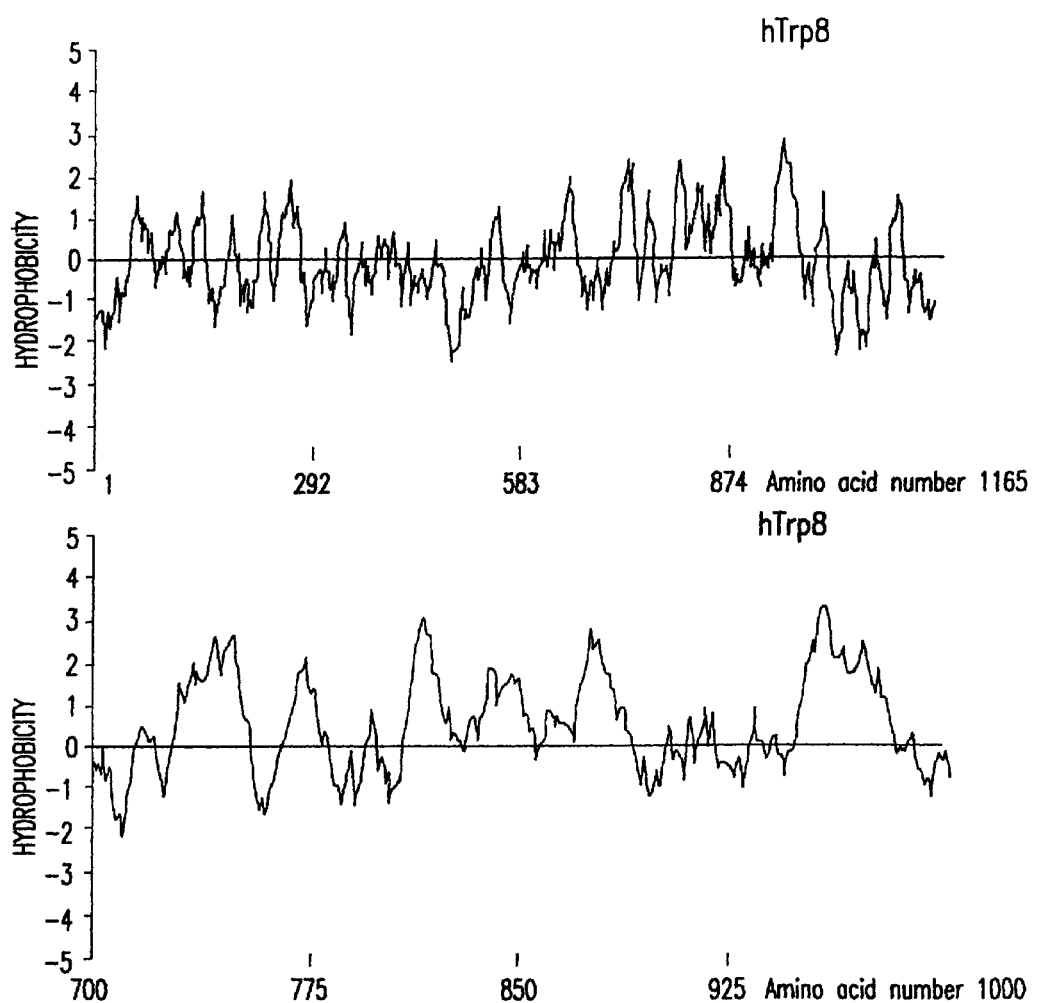

FIGS. 6A-C. Predicted topography of the TRP8 protein transient receptor potential channel in the membrane.

Figure 7:
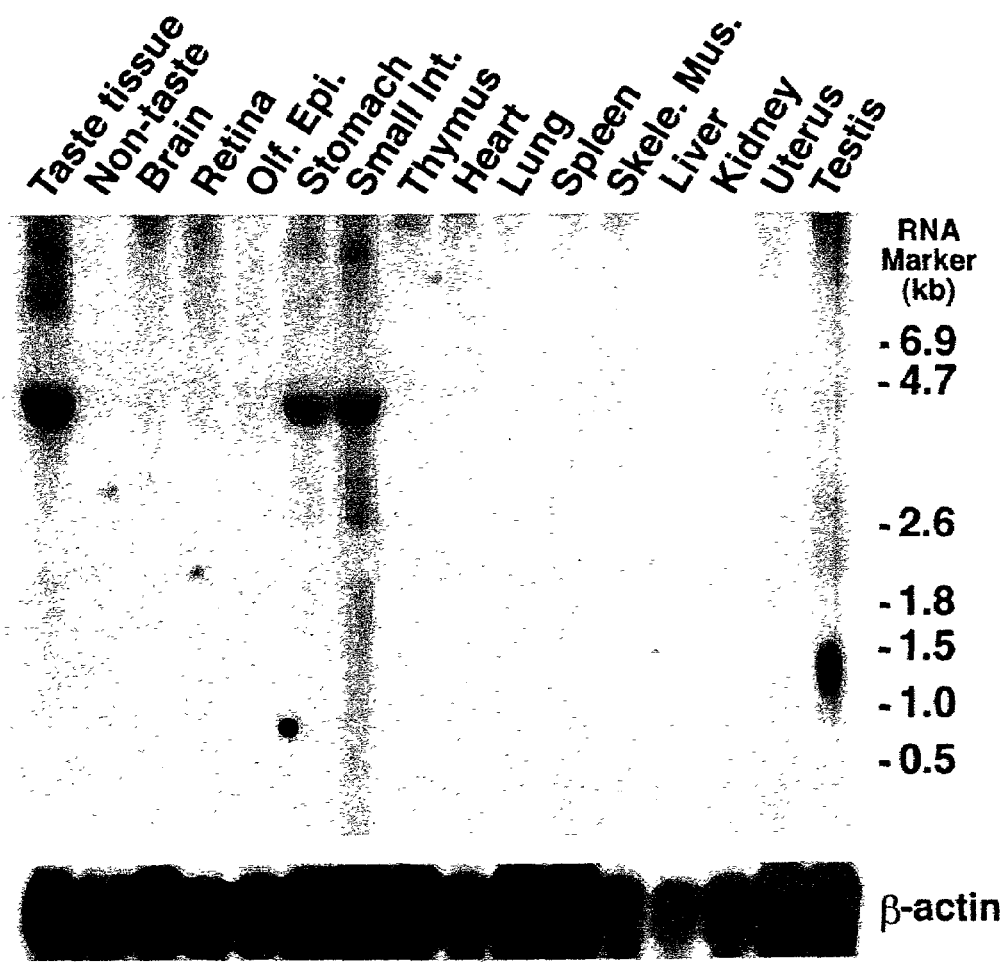

FIG. 7. Distribution of TRP8 mRNA and protein in mouse tissues. (a) Autoradiogram of a northern blot hybridized with a TRP8 cDNA probe. Each lane contained 25 μg total RNA isolated from the following mouse tissues: circumvallate and foliate papillae-enriched taste tissue (Taste tissue), lingual tissue devoid of taste buds (Non-taste), brain, retina, olfactory epithelium (Olf. Epi.), stomach, small intestine (Small Int.), thymus, heart, lung, spleen, skeletal muscle (Skele. Mus.), liver, kidney, uterus and testis. A 4.5 kb transcript was detected in taste tissue, stomach and small intestine, and to a much lesser extent, in uterus and testis. To control for MRNA quantity the same blot was stripped and reprobed with a β-actin cDNA probe (lower panel). The size in kilobases (kb) of RNA markers is indicated at the right-hand side. (b) Autoradiogram of a western blot probed with an anti-TRP8 antibody. Protein extracts (50 μg) prepared from the murine tissues indicated were electrophoresed, transferred to a nitrocellulose membrane, then the blot incubated with an antibody against the carboxyl-terminal of TRP8. Immunoreactive protein of ~130 kD, the predicted molecular weight of TRP8, was detected in stomach and small intestine; a higher molecular weight species was identified in liver and kidney. Molecular size markers are given in kilodaltons.

FIG. 8. TRP8 mRNA is expressed in taste receptor cells. Sections of murine lingual epithelia containing circumvallate and foliate papillae were hybridized with $^{33}$P-labeled antisense RNA probes for TRP8 (a,c) and α-gustducin (d), and subjected to autoradiography. Photomicrographs of circumvallate (a) and foliate (b) papillae hybridized to the antisense TRP8 probe demonstrates expression of TRP8 in a subset of TRCs. (d) Shows hybridization of an α-gustducin antisense probe to foliate papillae. Hybridization controls with sense probes showed the absence of non-specific binding of the TRP8 probe (b) or the α-Gustducin probe (e).

Figure 9H:
Figure 9I:
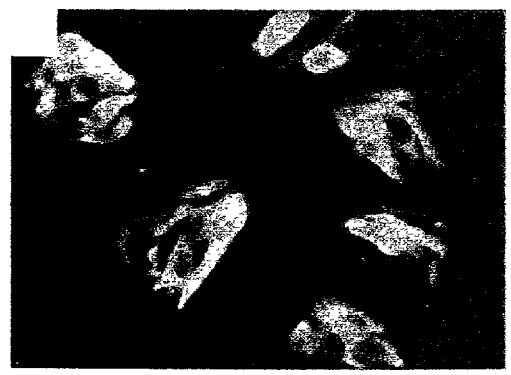

FIG. 9. Co-localization in TRCs of TRP8 and other signal transduction elements. Immunofluorescence of Gγ13 (a) and TRP8 (b) in the same longitudinal section of mouse taste papillae section: (c) is the overlay of a and b. Immunofluorescence of TRP8 (d) and α-gustducin (e) in the same section: (f) is the overlay of d and e. Immunofluorescence of PLCβ2 (g) and TRP8 (h) in the same section: (i) is the overlay of g and h.

Figure 10:
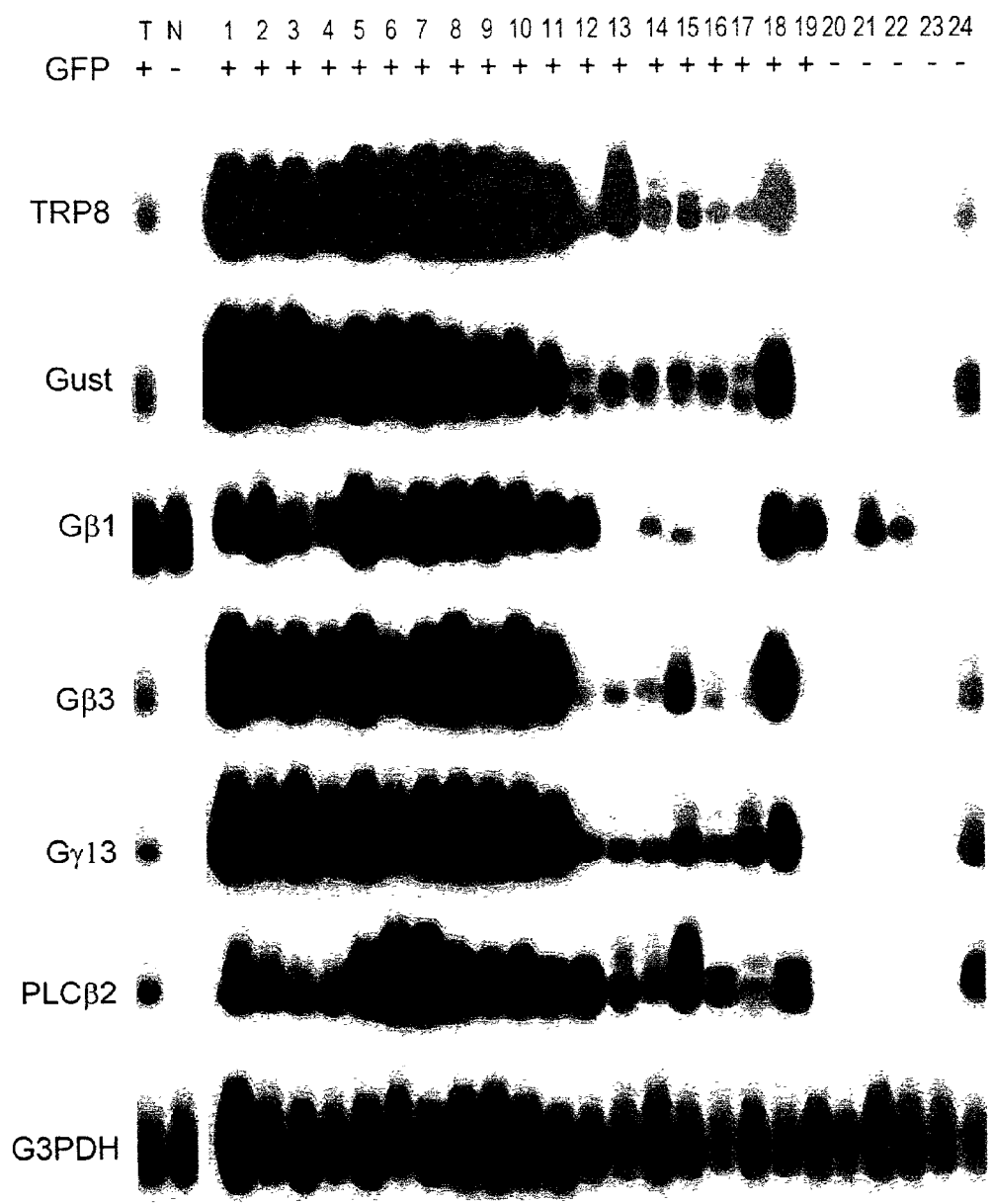

FIG. 10. Profiling the pattern of expression of TRP8, a-gustducin, Gβ1, Gβ3, Gγ13 and PLCβ2 in taste tissue and taste cells. Left panel: Southern hybridization to RT-PCR products from murine taste tissue (T) and control non-taste lingual tissue (N). 3'-region probes from TRP8, α-gustducin (Gust), Gβ1, Gβ3, Gγ13, PLCβ2 and glyceraldehyde 3-phosphate dehydrogenase (G3PDH) were used to probe the blots. Note that TRP8, α-gustducin, Gβ1, Gβ3, Gγ13 and PLCβ2 were all expressed in taste tissue, but not in non-taste tissue. Right panel: Southern hybridization to RT-PCR products from 24 individually amplified taste receptor cells from a transgenic mouse expressing green fluorescent protein (GFP) from the gustducin promoter. 19 cells were GFP-positive (+), 5 cells were GFP-negative (–). Expression of TRP8, α-gustducin, Gβ3, Gγ13and PLCβ2 was fully coincident. 15 of 19 TRP8-positive cells were also positive for Gβ1. G3PDH served as a positive control to demonstrate successful amplification of products.

Figure 11:
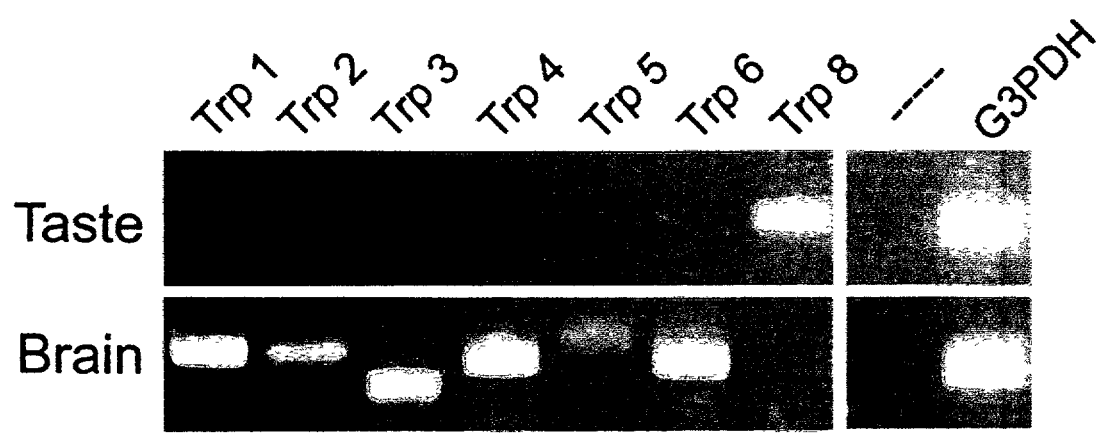

FIG. 11. TRP8, but not mTrp 1-7, is detected by PCR in taste tissue. PCR amplifications of TRP8 and mTrp 1-7 were performed using non-degenerate primers specific for each Trp family member. Taste cDNA (upper panels) and brain cDNA (lower panels) provided templates for amplification. Amplified material was resolved in a 1.2% agarose gel. Bands of the expected molecular weight were sequenced to verify the identity of the Trp channel amplified. Positive (G3PDH primers) and negative (no primers) controls are shown (right panels).

FIG. 12. Heterologous expression of TRP8. Xenopus oocytes were injected with 50 ng of TRP8 cRNA (a) or 50 nl of water (b); two days after injection, oocytes were treated with thapsigargin (2 μM), followed by the addition of Ca++(10 mM) or EGTA as indicated (arrows). The traces represent currents induced at negative membrane potentials (command voltage −80 mV). (c) I-V curve for oocytes injected with TRP8 cRNA or water demonstrates a reversal potential, consistent with Ca++ activation of the endogenous calcium-activated chloride conductance (IC$l_{Ca}$). (d) The maximal inward current elicited with external Ca++ present in the bathing media for oocytes injected with TRP8 cRNA or water (control).

Figure 13:
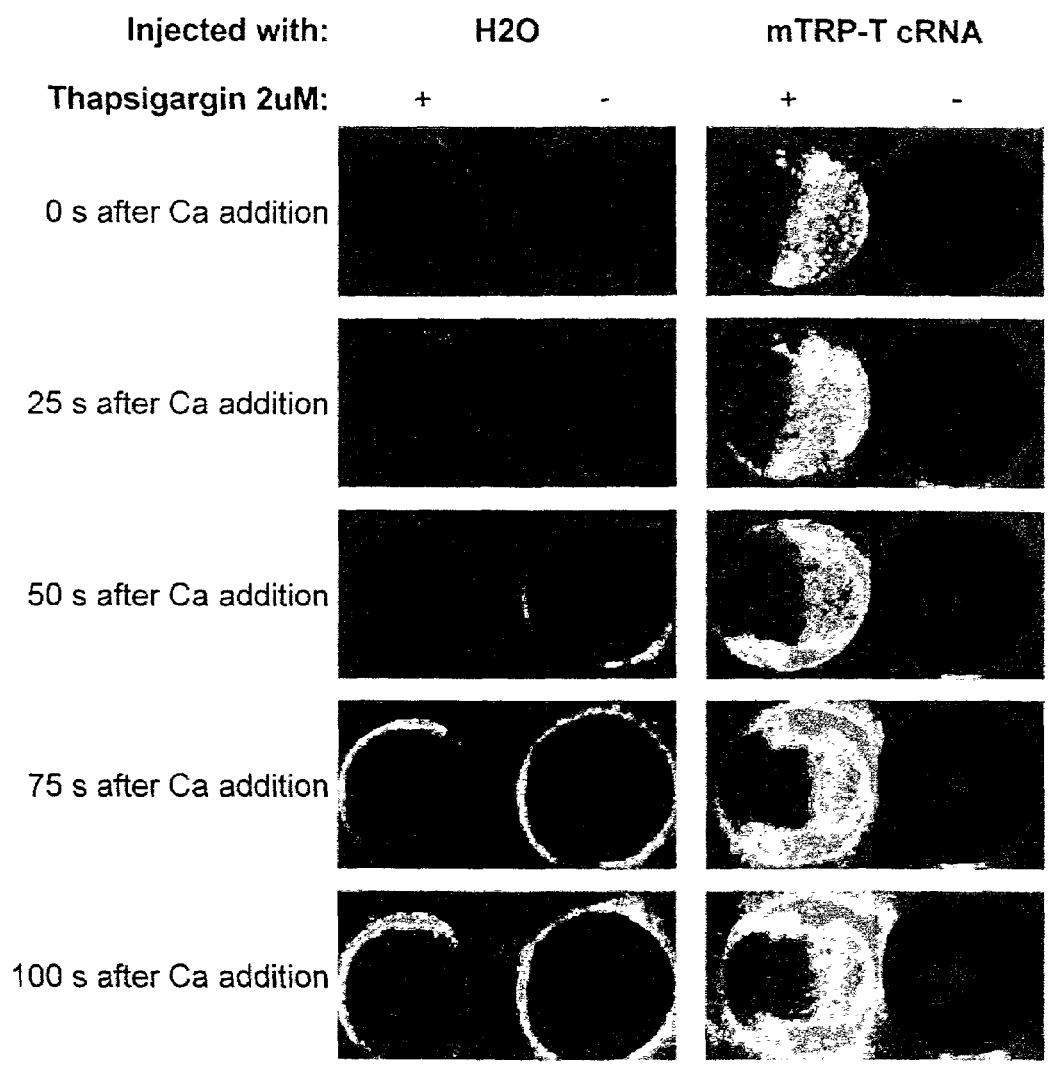

FIG. 13. TRP8 functions as a Ca++ channel. Xenopus oocytes were injected with 50 ng of TRP8 cRNA (right panels) or 50 nl of water (left panels); two days after injection, oocytes were treated with thapsigargin (2 μM), followed by the addition of Ca++ (10 mM).

Figure 14:
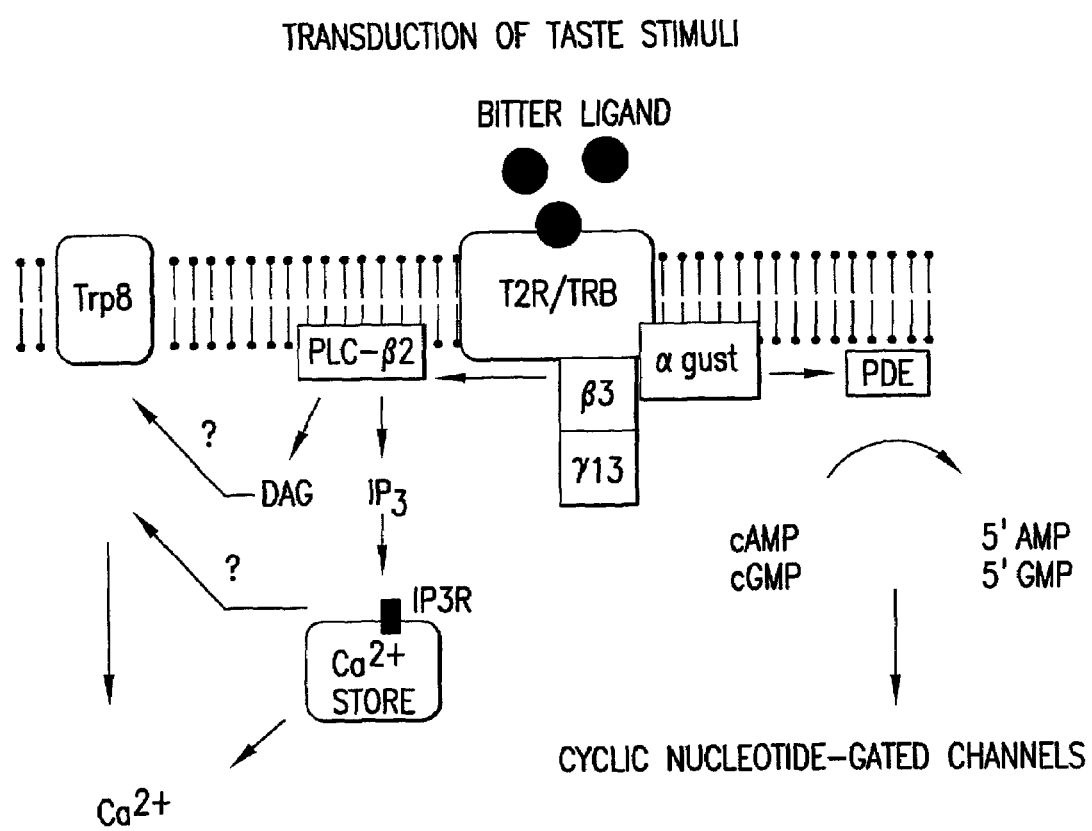

FIG. 14. Potential signal transduction pathways in TRCs utilizing TRP8. Responses to bitter compounds such as denatonium are initiated by binding to one or more gustducin-coupled receptors of the T2R/TBR family. Activation of the gustducin heterotrimer releases its βγmoiety (e.g. Gβ3/Gγ13) which stimulates PLCβ2, resulting in production of IP$_3$ and DAG. IP$_3$ binds to its receptors e.g. IP$_3$R3 and causes the release of Ca$^{++}$ from intracellular stores, triggering activation of TRP8 channels, which ultimately leads to the influx of Ca$^{++}$ through TRP8 channels. DAG may act directly on TRP8 to lead to Ca$^{++}$ influx. Artificial sweeteners may depend on a similar transduction pathway, but with sweet-responsive receptors, e.g., T1R3 coupled to gustducin or other G proteins initiating the signal that leads to the production of IP$_3$ and DAG and stimulation of TRP8.

5. DETAILED DESCRIPTION OF THE INVENTION

TRP8 is a channel protein that participates in receptor-mediated taste signal transduction and belongs to the family of calcium channel proteins known as transient receptor potential channels (Montell C., 1997, *Mol. Pharmacol.* 52:755-763) The present invention encompasses TRP8 nucleotides, TRP8 proteins and peptides, as well as antibodies to the TRP8 protein. The invention also relates to host cells and animals genetically engineered to express the TRP8 channel or to inhibit or "knock-out" expression of the animal's endogenous TRP8.

The invention further provides screening assays designed for the identification of modulators, such as agonists and antagonists, of TRP8 activity. The use of host cells that naturally express TRP8 or genetically engineered host cells and/or animals offers an advantage in that such systems allow the identification of compounds that affect the signal transduced by the TRP8 protein.

Various aspects of the invention are described in greater detail in the subsections below.

5.1. THE TRP8 GENE

The cDNA sequence and deduced amino acid sequence of murine TRP8 are shown in FIGS. 1 (SEQ ID NO: 1) and 2 (SEQ ID NO: 2), respectively. The cDNA and deduced ammo acid sequence of human TRP8 are shown in FIGS. 3 (SEQ ID NO: 3) and 4 (SEQ ID NO: 4), respectively.

The TRP8 nucleotide sequences of the invention include: (a) the DNA sequences shown in FIG. 1 (SEQ ID NO: 1) or 3 (SEQ ID NO: 3) or contained in the cDNA clone pMR24 within *E. coli* strain XL10 Gold as deposited with the American Type Culture Collection (ATCC Accession No. ); (b) nucleotide sequences t,hat encode the amino acid sequence shown in FIG. 2 (SEQ ID NO: 2) or 4 (SEQ ID NO: 4) or the TRP8 amino acid sequence encoded by the cDNA clone pMR24 as deposited with the ATCC; (c) any nucleotide sequence that (i) hybridizes to the nucleotide sequence set forth in (a) or (b) under stringent conditions, e.g., hybridization to filter-bound DNA in 0.5 M NaHPO$_4$, 7% sodium dodecyl sulfate (SDS), 1 mM EDTA at 65EC, and washing in 0.1×SSC/0.1% SDS at 68EC (Ausubel F.M. et al., eds., 1989, Current Protocols in Molecular Biology, Vol. I, Green Publishing Associates, Inc., and John Wiley & sons, Inc., New York, at p. 2.10.3) and (ii) encodes a functionally equivalent gene product; and (d) any nucleotide sequence that hybridizes to a DNA sequence that encodes the amino acid sequence shown in FIG. 1 (SEQ ID NO: 1) or 3 (SEQ ID NO: 3), or that is contained in cDNA clone pMR24 as deposited with the ATCC, under less stringent conditions, such as moderately stringent conditions, e.g., washing in 0.2×SSC/0.1% SDS at 42EC (Ausubel et al., 1989 supra), yet which still encodes a functionally equivalent TRP8 gene product. Functional equivalents of the TRP8 protein include naturally occurring TRP8 present in species other than mice and humans. The invention also includes degenerate variants of sequences (a) through (d). The invention also includes nucleic acid molecules, that may encode or act as TRP8 antisense molecules, useful, for example, in TRP8 gene regulation (for and/or as antisense primers in amplification reactions of TRP8 gene nucleic acid sequences).

In addition to the TRP8 nucleotide sequences described above, homologs of the TRP8 gene present in other species can be identified and readily isolated, without undue experimentation, by molecular biological techniques well known in the art. For example, cDNA libraries, or genomic DNA libraries derived from the organism of interest can be screened by hybridization using the nucleotides described herein as hybridization or amplification probes.

The invention also encompasses nucleotide sequences that encode mutant TRP8s, peptide fragments of the TRP8, truncated TRP8, and TRP8 fusion proteins. These include, but are not limited to nucleotide sequences encoding polypeptides or peptides corresponding to the TM (transmembrane) and/or CD (cytoplasmic) domains of TRP8 or portions of these domains; truncated TRP8s in which one or two of the domains is deleted, e.g., a functional TRP8 lacking all or a portion of the CD region. Certain of these truncated or mutant TRP8 proteins may act as dominant-negative inhibitors of the native TRP8 protein. Nucleotides encoding fusion proteins may include but are not limited to full length TRP8, truncated TRP8 or peptide fragments of TRP8 fused to an unrelated protein or peptide such as an enzyme, fluorescent protein, luminescent protein, ect., which can be used as a marker.

TRP8 nucleotide sequences may be isolated using a variety of different methods known to those skilled in the art. For example, a cDNA library constructed using RNA from a tissue known to express TRP8 can be screened using a labeled TRP8 probe. Alternatively, a genomic library may be screened to derive nucleic acid molecules encoding the TRP8 channel protein. Further, TRP8 nucleic acid sequences may be derived by performing PCR using two oligonucleotide primers designed on the basis of the TRP8 nucleotide sequences disclosed herein. The template for the reaction may be cDNA obtained by reverse transcription of mRNA prepared from cell lines or tissue known to express TRP8.

The invention also encompasses (a) DNA vectors that contain any of the foregoing TRP8 sequences and/or their complements (i.e., antisense); (b) DNA expression vectors that contain any of the foregoing TRP8 sequences operatively associated with a regulatory element that directs the expression of the TRP8 coding sequences; (c) genetically engineered host cells that contain any of the foregoing TRP8 sequences operatively associated with a regulatory element that directs the expression of the TRP8 coding sequences in the host cell; and (d) transgenic mice or other organisms that contain any of the foregoing TRP8 sequences. As used herein, regulatory elements include but are not limited to inducible and non-inducible promoters, enhancers, operators and other elements known to those skilled in the art that drive and regulate expression.

5.2. TRP8 PROTEINS AND POLYPEPTIDES

TRP8 protein, polypeptides and peptide fragments, mutated, truncated or deleted forms of the TRP8 and/or TRP8 fusion proteins can be prepared for a variety of uses, including but not limited to the generation of antibodies, the identification of other cellular gene products involved in the regulation of TRP8 mediated taste perception, and the screening for compounds that can be used to modulate taste perception such as bitter blocking agents and taste modifiers.

FIGS. 2 (SEQ ID NO: 2) and 4 (SEQ ID NO: 4) show the deduced amino acid sequence of the murine and human TRP8 protein, respectively. The TRP8 amino acid sequences of the invention include the amino acid sequence shown in FIG. 2 (SEQ ID NO: 2) or FIG. 4 (SEQ ID NO: 4), or the amino acid sequence encoded by cDNA clone pMR24 as deposited with the ATCC. Further, TRP8s of other species are encompassed by the invention. In fact, any TRP8 protein encoded by the TRP8 nucleotide sequences described in Section 5.1, above, is within the scope of the invention.

The invention also encompasses proteins that are functionally equivalent to the TRP8 encoded by the nucleotide sequences described in Section 5.1, as judged by any of a number of criteria, including but not limited to the ability of a bitter tastant to trigger the influx of calcium from extracellular calcium stores into a taste receptor cell expressing said protein, leading to transmitter release from the taste receptor cell into the synapse and activation of an afferent nerve. Such functionally equivalent TRP8 proteins include but are not limited to proteins having additions or substitutions of amino acid residues within the amino acid sequence encoded by the TRP8 nucleotide sequences described, above, in Section 5.1, but which result in a silent change, thus producing a functionally equivalent gene product.

Peptides corresponding to one or more domains of TRP8 (e.g., transmembrane (TM) or cellular domain (CD)), truncated or deleted TRP8s (e.g., TRP8 in which the TM and/or CD is deleted) as well as fusion proteins in which the full length TRP8, a TRP8 peptide or a truncated TRP8 is fused to an unrelated protein are also within the scope of the invention and can be designed on the basis of the TRP8 nucleotide and TRP8 amino acid sequences disclosed herein. Such fusion proteins include fusions to an enzyme, fluorescent protein, or luminescent protein which provide a marker function.

While the TRP8 polypeptides and peptides can be chemically synthesized (e.g, see Creighton, 1983, Proteins: Structures and Molecular Principles, W.H. Freeman & Co., N.Y.), large polypeptides derived from TRP8 and the full length TRP8 itself may be advantageously produced by recombinant DNA technology using techniques well known in the art for expressing a nucleic acid containing TRP8 gene sequences and/or coding sequences. Such methods can be used to construct expression vectors containing the TRP8 nucleotide sequences described in Section 5.1 and appropriate transcriptional and translational control signals. These methods include, for example, in vitro recombinant DNA techniques, synthetic techniques, and in vivo genetic recombination. (See, for example, the techniques described in Sambrook et al., 1989, supra, and Ausubel et al., 1989, supra).

A variety of host-expression vector systems may be utilized to express the TRP8 nucleotide sequences of the invention. Where the TRP8 peptide or polypeptide is expressed as a soluble derivative (e.g., peptides corresponding to TM and/or CD) and is not secreted, the peptide or polypeptide can be recovered from the host cell. Alternatively, where the TRP8 peptide or polypeptide is secreted the peptide or polypeptides may be recovered from the culture media. However, the expression systems also include engineered host cells that express TRP8 or functional equivalents, anchored in the cell membrane. Purification or enrichment of the TRP8 from such expression systems can be accomplished using appropriate detergents and lipid micelles and methods well known to those skilled in the art. Such engineered host cells themselves may be used in situations where it is important not only to retain the structural and functional characteristics of the TRP8, but to assess biological activity, i.e., in drug screening assays.

The expression systems that may be used for purposes of the invention include but are not limited to microorganisms such as bacteria transformed with recombinant bacteriophage, plasmid or cosmid DNA expression vectors containing TRP8 nucleotide sequences; yeast transformed with recombinant yeast expression vectors containing TRP8 nucleotide sequences or mammalian cell systems harboring recombinant expression constructs containing promoters derived from the genome of mammalian cells or from mammalian viruses.

Appropriate expression systems can be chosen to ensure that the correct modification, processing and sub-cellular localization of the TRP8 channel protein occurs. To this end, eukaryotic host cells which possess the ability to properly modify and process the TRP8 channel protein are preferred. For long-term, high yield production of recombinant TRP8 channel protein, such as that desired for development of cell lines for screening purposes, stable expression is preferred. Rather than using expression vectors which contain origins of replication, host cells can be transformed with DNA controlled by appropriate expression control elements and a selectable marker gene, i.e., tk, hgprt, dhfr, neo, and hygro gene, to name a few. Following the introduction of the foreign DNA, engineered cells may be allowed to grow for 1-2 days in enriched media, and then switched to a selective media. Such engineered cell lines may be particularly useful in screening and evaluation of compounds that modulate the endogenous activity of the TRP8 gene product.

5.3. TRANSGENIC ANIMALS

The TRP8 gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate TRP8 transgenic animals.

Any technique known in the art may be used to introduce the TRP8 transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, *Proc. Natl. Acad. Sci. USA* 82:6148-6152); gene targeting in embryonic stem cells (Thompson et al., 1989, *Cell,* 56:313-321); electroporation of embryos (Lo, 1983, *Mol Cell. Biol.* 3:1803-1814); and sperm-mediated gene transfer (Lavitrano et al., 1989, *Cell* 57:717-723); etc. For a review of such techniques, see Gordon, 1989, *Transgenic Animals, Intl. Rev. Cytol.* 115:171-229, which is incorporated by reference herein in its entirety.

The present invention provides for transgenic animals that carry the TRP8 transgene in all their cells, as well as animals which carry the transgene in some, but not all their cells, i.e., mosaic animals. The transgene may also be selectively introduced into and activated in a particular cell type by following, for example, the teaching of Lasko et al., (Lasko, M. et al., 1992, *Proc. Natl. Acad. Sci. USA* 89:6232-6236). The regulatory sequences required for such a cell-type specific activation will depend upon the particular cell type of interest, and will be apparent to those of skill in the art. When it is desired that the TRP8 transgene be integrated into the chromosomal site of the endogenous TRP8 gene, gene targeting is preferred. Briefly, when such a technique is to be utilized, vectors containing some nucleotide sequences homologous to the endogenous TRP8 gene are designed for the purpose of integrating, via homologous recombination with chromosomal sequences, into and disrupting the function of the nucleotide sequence of the endogenous TRP8 gene.

Once transgenic animals have been generated, the expression of the recombinant TRP8 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of TRP8 gene-expressing tissue may also be evaluated immunocytochemically using antibodies specific for the TRP8 transgene product.

5.4. ANTIBODIES TO TRP8 PROTEINS

Antibodies that specifically recognize one or more epitopes of TRP8, or epitopes of conserved variants of TRP8, or peptide fragments of TRP8 are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in conjunction with compound screening schemes, as described, below, in Section 5.5, for the evaluation of the effect of test compounds on expression and/or activity of the TRP8 gene product.

For production of antibodies, various host animals may be immunized by injection with a TRP8 protein, or TRP8 peptide. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG-(Bacille Calmette-Guerin) and *Corynebacterium parvum*.

Polyclonal antibodies comprising heterogeneous populations of antibody molecules, may be derived from the sera of the immunized animals. Monoclonal antibodies may be obtained by any technique which provides for the production of antibody molecules by continuous cell lines in culture. These include, but are not limited to, the hybridoma technique of Kohler and Milstein, (1975, *Nature* 256:495-497; and U.S. Pat. No. 4,376,110), the human B-cell hybridoma technique (Kosbor et al., 1983, *Immunology Today* 4:72; Cole et al., 1983, *Proc. Natl. Acad. Sci.* USA 80:2026-2030), and the EBV-hybridoma technique (Cole et al., 1985, *Monoclonal Antibodies And Cancer Therapy*, Alan R. Liss, Inc., pp. 77-9). Such antibodies may be of any immunoglobulin class including IgG, IgM, IgE, IgA, IgD and any subclasses thereof. The hybridoma producing the mAb of this invention may be cultivated in vitro or in vivo. Production of high titres of Mabs in vivo makes this the presently preferred method of production.

In addition, techniques developed for the production of "chimeric antibodies" by splicing the genes from a mouse antibody molecule of appropriate antigen specificity together with genes from a human antibody molecule of appropriate biological activity can be used (Morrison et al., 1984, *Proc. Nat'l. Acad. Sci.*, 81:6851-6855; Neuberger et al., 1984, *Nature*, 312: 604-608; Takeda et al. 1985, *Nature* 314: 452-454). Alternatively, techniques developed for the production of humanized antibodies (U.S. Pat. No. 5,585,089) or single chain antibodies (U.S. Pat. No. 4,946,778 Bird, 1988, *Science* 242: 423-426; Huston et al., 1988, *Proc. Nat'l. Acad. Sci USA*, 85: 5879-5883; and Ward et al., 1989, *Nature* 334: 544-546) may be used to produce antibodies that specifically recognize one or more epitopes of TRP8.

5.5. SCREENING ASSAYS FOR DRUGS AND OTHER CHEMICAL COMPOUNDS USEFUL IN REGULATION OF TASTE PERCEPTION

The present invention relates to screening assay systems designed to identify compounds or compositions that modulate TRP8 activity or TRP8 gene expression, and thus, may be useful for modulation of bitter taste perception.

In accordance with the invention, a cell-based assay system can be used to screen for compounds that modulate the activity of the TRP8 and thereby, modulate the perception of bitterness. To this end, cells that endogenously express TRP8 can be used to screen for compounds. Alternatively, cell lines, such as 293 cells, COS cells, CHO cells, fibroblasts, and the like, genetically engineered to express TRP8 can be used for screening purposes. Preferably, host cells genetically engineered to express a functional TRP8 are those that respond to activation by bitter tastants, such as taste receptor cells. Further, ooyctes or liposomes engineered to express the TRP8 channel protein may be used in assays developed to identify modulators of TRP8 activity.

The present invention provides for methods for identifying a compound that induces the perception of a bitter taste (a "bitterness activator") comprising (i) contacting a cell expressing the TRP8 channel protein with a test compound and measuring the level of TRP8 activation; (ii) in a separate experiment, contacting a cell expressing the TRP8 channel protein with a vehicle control and measuring the level of TRP8 activation where the conditions are essentially the same as in part (i), and then (iii) comparing the level of activation of TRP8 measured in part (i) with the level of activation of TRP8 in part (ii), wherein an increased level of activated TRP8 in the presence of the test compound indicates that the test compound is a TRP8 activator.

The present invention also provides for methods for identifying a compound that inhibits the perception of a bitter taste (a "bitterness inhibitor") comprising (i) contacting a cell expressing the TRP8 channel protein with a test compound in the presence of a bitter tastant and measuring the level of TRP8 activation; (ii) in a separate experiment, contacting a cell expressing the TRP8 channel protein with a bitter tastant and measuring the level of TRP8 activation, where the conditions are essentially the same as in part (i) and then (iii) comparing the level of activation of TRP8 measured in part (i) with the level of activation of TRP8 in part (ii), wherein a decrease level of activation of TRP8 in the presence of the test compound indicates that the test compound is a TRP8 inhibitor.

A "bitter tastant", as defined herein, is a compound or molecular complex that induces, in a subject, the perception of a bitter taste. In particular, a bitter tastant is one which results in the activation of the TRP8 channel protein resulting in an influx of $Ca^{+2}$ into the cell. Examples of bitter tastants include but are not limited to denatonium benzoate ("denatonium"; also "DEN"), quinine hydrochloride ("quinine"; also "QUI"), strychnine hydrochloride ("strychnine";

also "STR"), nicotine hemisulfate ("nicotine"; also "NIC"), atropine hydrochloride ("atropine"; also "ATR"), sparteine, naringin, caffeic acid("caffeine"; also "CAF"), quinacrine, and epicatechin. See Ming et al., 1999, *Proc. Natl. Acad. Sci. U.S.A.* 96:9903-9908, incorporated by reference herein.

In utilizing such cell systems, the cells expressing the TRP8 channel protein are exposed to a test compound or to vehicle controls (e.g., placebos). After exposure, the cells can be assayed to measure the expression and/or activity of components of the signal transduction pathway of TRP8, or the activity of the signal transduction pathway itself can be assayed.

The ability of a test molecule to modulate the activity of TRP8 may be measured using standard biochemical and physiological techniques. Responses such as activation or suppression of catalytic activity, phosphorylation or dephosphorylation of TRP8 and/or other proteins, activation or modulation of second messenger production, changes in cellular ion levels, association, dissociation or translocation of signaling molecules, or transcription or translation of specific genes may be monitored. In non-limiting embodiments of the invention, changes in intracellular $Ca^{2+}$ levels may be monitored by the fluorescence of indicator dyes such as indo, fura, etc. In addition activation of cyclic nucleotide phosphodiesterase, adenylate cyclase, phospholipases ATPases and $Ca^{2+}$ sensitive release of neurotransmitters may be measured to identify compounds that modulate TRP8 signal transduction. Further, changes in membrane potential resulting from modulation of the TRP8 channel protein can be measured using a voltage clamp or patch recording methods.

For example, after exposure to a test compound, cell lysates can be assayed for increased intracellular levels of $Ca^{2+}$ and activation of calcium dependent down stream messengers such as phosphodiesterase, phospholipases, ATPases or cAMP. The ability of a test compound to increase intracellular levels of $Ca^{2+}$ and activate phosphodiesterase or decrease cAMP levels compared to those levels seen with cells treated with a vehicle control, indicates that the test compound acts as an agonist (i.e., is a TRP8 activator) and induces signal transduction mediated by the TRP8 expressed by the host cell. The ability of a test compound to inhibit bitter tastant induced calcium influx and inhibit phosphodiesterase or increase cAMP levels compared to those levels seen with a vehicle control indicates that the test compound acts as an antagonist (i.e., is a TRP8 inhibitor) and inhibits signal transduction mediated by TRP8.

In a specific embodiment of the invention, levels of cAMP can be measured using constructs containing the cAMP responsive element linked to any of a variety of different reporter genes. Such reporter genes may include but are not limited to chloramphenicol acetyltransferase (CAT), luciferase, β-glucuronidase (GUS), growth hormone, or placental alkaline phosphatase (SEAP). Such constructs are introduced into cells expressing TRP8 channel protein thereby providing a recombinant cell useful for screening assays designed to identify modulators of TRP8 activity.

Following exposure of the cells to the test compound, the level of reporter gene expression may be quantitated to determine the test compound's ability to regulate TRP8 activity. Alkaline phosphatase assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemilumenscent assays such as those described in Bronstein, I. et al. (1994, *Biotechniques* 17: 172-177). Such assays provide a simple, sensitive easily automatable detection system for pharmaceutical screening.

Additionally, to determine intracellular cAMP concentrations, a scintillation proximity assay (SPA) may be utilized (SPA kit is provided by Amersham Life Sciences, Illinois). The assay utilizes $^{125}$I-label cAMP, an anti-cAMP antibody, and a scintillant-incorporated microsphere coated with a secondary antibody. When brought into close proximity to the microsphere through the labeled cAMP-antibody complex, $^{125}$I will excite the scintillant to emit light. Unlabeled cAMP extracted from cells competes with the $^{125}$I-labeled cAMP for binding to the antibody and thereby diminishes scintillation. The assay may be performed in 96-well plates to enable high-throughput screening and 96 well-based scintillation counting instruments such as those manufactured by Wallac or Packard may be used for readout.

In yet another embodiment of the invention, levels of intracellular $Ca^{2+}$ can be monitored using $Ca^{2+}$ indication dyes, such as Fluo-3 and Fura-Red using methods such as those described in Komuro and Rakic, 1998, In: *The Neuron in Tissue Culture*. L.W. Haymes, Ed. Wiley, New York.

Test activators which activate the activity of TRP8, identified by any of the above methods, may be subjected to further testing to confirm their ability to induce a bitterness perception. Test inhibitors which inhibit the activation of TRP8 by bitter tastants, identified by any of the above methods, may then be subjected to further testing to confirm their inhibitory activity. The ability of the test compound to modulate the activity of the TRP8 receptor may be evaluated by behavioral, physiologic, or in vitro methods.

For example, a behavioral study may be performed where a test animal may be offered the choice of consuming a composition comprising the putative TRP8 inhibitor and the same composition without the added compound. A preference for the composition comprising a test compound, indicated, for example, by greater consumption, would have a positive correlation with TRP8 inhibitory activity. Additionally, avoidance by a test animal of food containing a putative activator of TRP8 would have a positive correlation with the identification of an bitterness activator.

In addition to cell based assays, non-cell based assay systems may be used to identify compounds that interact with, e.g., bind to TRP8. Such compounds may act as antagonists or agonists of TRP8 activity and may be used to regulate bitter taste perception.

To this end, soluble TRP8 may be recombinantly expressed and utilized in non-cell based assays to identify compounds that bind to TRP8. The recombinantly expressed TRP8 polypeptides or fusion proteins containing one or more of the domains of TRP8 prepared as described in Section 5.2, infra, can be used in the non-cell based screening assays. For example, peptides corresponding to one or more of the cytoplasmic or transmembrane domains of TRP8, or fusion proteins containing one or more of the cytoplasmic or transmembrane domains of TRP8 can be used in non-cell based assay systems to identify compounds that bind to the cytoplasmic portion of the TRP8; such compounds may be useful to modulate the signal transduction pathway of the TRP8. In non-cell based assays the recombinantly expressed TRP8 may be attached to a solid substrate such as a test tube, microtitre well or a column, by means well known to those in the art (see Ausubel et al., ura). The test compounds are then assayed for their ability to bind to the TRP8.

The TRP8 channel protein may be one which has been fully or partially isolated from other molecules, or which may be present as part of a crude or semi-purified extract. As a non-limiting example, the TRP8 channel protein may be present in a preparation of taste receptor cell membranes. In particular embodiments of the invention, such taste receptor cell membranes may be prepared as set forth in Ming, D. et al., 1998, *Proc. Natl. Sci. U.S.A.* 95:8933-8938, incorporated by reference herein. Specifically, bovine circumvallate papillae ("taste tissue", containing taste receptor cells), may be hand dissected, frozen in liquid nitrogen, and stored at −80° C. prior to use. The collected tissues may then be homogenized with a Polytron homogenizer (three cycles of 20 seconds each at 25,000 RPM) in a buffer containing 10 mM Tris at pH 7.5, 10% vol/vol glycerol, 1 mM EDTA, 1 mM DTT, 10 µg/µl pepstatin A, 10 µg/µl leupeptin, 10 µg/µl aprotinin, and 100 µM 4-(2-amino ethyl) benzenesulfoyl fluoride hydrochloride. After particulate removal by centrifugation at 1,500×g for 10 minutes, taste membranes may be collected by centrifugation at 45,000×g for 60 minutes. The pelleted membranes may then be rinsed twice, re-suspended in homogenization buffer lacking protease inhibitors, and further homogenized by 20 passages through a 25 gauge needle. Aliquots may then be either flash frozen or stored on ice until use. As another non-limiting example, the taste receptor may be derived from recombinant clones (see Hoon, M. R. et al., 1999 *Cell* 96, 541-551).

Assays may also be designed to screen for compounds that regulate TRP8 expression at either the transcriptional or translational level. In one embodiment, DNA encoding a reporter molecule can be linked to a regulatory element of the TRP8 gene and used in appropriate intact cells, cell extracts or lysates to identify compounds that modulate TRP8 gene expression. Appropriate cells or cell extracts are prepared from any cell type that normally expresses the TRP8 gene, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

To identify compounds that regulate TRP8 translation, cells or in vitro cell lysates containing TRP8 transcripts may be tested for modulation of TRP8 mRNA translation. To assay for inhibitors of TRP8 translation, test compounds are assayed for their ability to modulate the translation of TRP8 mRNA in in vitro translation extracts.

In addition, compounds that regulate TRP8 activity may be identified using animal models. Behavioral, physiological, or biochemical methods may be used to determine whether TRP8 activation has occurred. Behavioral and physiological methods may be practiced in vivo. As an example of a behavioral measurement, the tendency of a test animal to voluntarily ingest a composition comprising the bitter tastant, in the presence or absence of test inhibitor, may be measured. If the bitter tastant activates TRP8 in the animal, the animal may be expected to experience a bitter taste, which would discourage it from ingesting more of the composition. If the animal is given a choice of whether to consume a composition containing bitter tastant only (with activated TRP8) or a composition containing bitter tastant together with a bitterness inhibitor (with lower levels of activated TRP8), it would be expected to prefer to consume the composition containing the bitterness inhibitor. Thus, the relative preference demonstrated by the animal inversely correlates with the activation of the TRP8 channel.

Physiological methods include nerve response studies, which may be performed using a nerve operably joined to a taste receptor cell containing tissue, in vivo or in vitro. Since exposure to bitter tastant which results in TRP8 activation may result in an action potential in taste receptor cells that is then propagated through a peripheral nerve, measuring a nerve response to a bitter tastant is, inter alia, an indirect measurement of TRP8 activation. An example of nerve response studies performed using the glossopharyngeal nerve are described in Ninomiya, Y., et al., 1997, *Am. J. Physiol.* (London) 272:R1002-R1006.

The assays described above can identify compounds which modulate TRP8 activity. For example, compounds that affect TRP8 activity include but are not limited to compounds that bind to the TRP8, and either activate signal transduction (agonists) or block activation (antagonists). Compounds that affect TRP8 gene activity (by affecting TRP8 gene expression, including molecules, e.g., proteins or small organic molecules, that affect transcription or interfere with splicing events so that expression of the full length or the truncated form of the TRP8 can be modulated) can also be identified using the screens of the invention. However, it should be noted that the assays described can also identify compounds that modulate TRP8 signal transduction e.g., compounds which affect downstream signaling events, such as inhibitors or enhancers of G protein activities which participate in transducing the signal activated by tastants binding to their receptor). The identification and use of such compounds which affect signaling events downstream of TRP8 and thus modulate effects of TRP8 on the perception of taste are within the scope of the invention.

The compounds which may be screened in accordance with the invention include, but are not limited to, small organic or inorganic compounds, peptides, antibodies and fragments thereof, and other organic compounds (e.g, peptidomimetics) that bind to TRP8 and either mimic the activity triggered by the natural tastant ligand (i.e., agonists) or inhibit the activity triggered by the natural ligand (i.e., antagonists).

Compounds may include, but are not limited to, peptides such as, for example, soluble peptides, including but not limited to members of random peptide libraries (see, e.g., Lam, K. S. et al., 1991, Nature 354:82-84; Houghten, R. et al., 1991, Nature 354:84-86); and combinatorial chemistry-derived molecular library made of D- and/or L- configuration amino acids, phosphopeptides (including, but not limited to, members of random or partially degenerate, directed phosphopeptide libraries; (see, e.g., Songyang, Z. et al., 1993, Cell 72:767-778), antibodies (including, but not limited to, polyclonal, monoclonal, humanized, anti-idiotypic, chimeric or single chain antibodies, and FAb, F(ab')₂ and FAb expression library fragments, and epitope binding fragments thereof), and small organic or inorganic molecules.

Other compounds which may be screened in accordance with the invention include but are not limited to small organic molecules that affect the expression of the TRP8 gene or some other gene involved in the TRP8 signal transduction pathway e.g., by interacting with the regulatory region or transcription factors involved in gene expression); or such compounds that affect the activity of the TRP8 or the activity of some other intracellular factor involved in the TRP8 signal transduction pathway, such as, for example, a TRP8 associated G-protein.

5.6. COMPOSITIONS CONTAINING MODULATORS OF TRP8 AND THEIR USES

The present invention provides for methods of inhibiting a bitter taste resulting from contacting a taste tissue of a subject with a bitter tastant, comprising administering to the subject an effective amount of a TRP8 inhibitor, such as a TRP8 inhibitor identified by measuring TRP8 activation as set forth in Section 5.5 supra. The present invention also provides for methods of inhibiting a bitter taste of a composition, comprising incorporating, in the composition, an effective amount of a TRP8 inhibitor. An "effective amount" of the TRP8 inhibitor is an amount that subjectively decreases the perception of bitter taste and/or that is associated with a detectable decrease in TRP8 activation as measured by one of the above assays.

The present invention further provides for a method of producing the perception of a bitter taste by a subject, comprising administering, to the subject, a composition comprising a compound that activates TRP8 activity such as a bitterness activator identified as set forth in Section 5.5 supra. The composition may comprise an amount of activator that is effective in producing a taste recognized as bitter by a subject.

Accordingly, the present invention provides for compositions comprising bitterness activators and bitterness inhibitors. Such compositions include any substances which may come in contact with taste tissue of a subject, including but not limited to foods, beverages, pharmaceuticals, dental products, cosmetics, and wetable glues used for envelopes and stamps.

In one set of embodiments, a bitterness inhibitor is used to counteract the perception of bitterness associated with a co-present bitter tastant. In these embodiments, a composition of the invention comprises a bitter tastant and a bitterness inhibitor, where the bitterness inhibitor is present at a concentration which inhibits bitter taste perception. For example, when the concentration of bitter tastant in the composition and the concentration of bitterness inhibitor in the composition are subjected to an assay as disclosed in Section 5.1 supra, the bitterness inhibitor inhibits the activation of TRP8 by the bitter tastant.

The present invention may be used to improve the taste of foods by decreasing or eliminating the aversive effects of bitter tastants. If a bitter tastant is a food preservative, the TRP8 inhibitors of the invention may permit or facilitate its incorporation into foods, thereby improving food safety. For foods administered as nutritional supplements, the incorporation of TRP8 inhibitors of the invention may encourage ingestion, thereby enhancing the effectiveness of these compositions in providing nutrition or calories to a subject.

The TRP8 inhibitors of the invention may be incorporated into medical and/or dental compositions. Certain compositions used in diagnostic procedures have an unpleasant taste, such as contrast materials and local oral anesthetics. The TRP8 inhibitors of the invention may be used to improve the comfort of subjects undergoing such procedures by improving the taste of compositions. In addition, the TRP8 inhibitors of the invention may be incorporated into pharmaceutical compositions, including tablets and liquids, to improve their flavor and improve patient compliance (particularly where the patient is a child or a non-human animal).

The TRP8 inhibitors of the invention may be comprised in cosmetics to improve their taste features. For example, but not by way of limitation, the TRP8 inhibitors of the invention may be incorporated into face creams and lipsticks. In addition, the TRP8 inhibitors of the invention may be incorporated into compositions that are not traditional foods, beverages, pharmaceuticals, or cosmetics, but which may contact taste membranes. Examples include, but are not limited to, soaps, shampoos, toothpaste, denture adhesive, glue on the surfaces of stamps and envelopes, and toxic compositions used in pest control (e.g., rat or cockroach poison).

6. EXAMPLE

CLONING AND CHARACTERIZATION OF THE TRP8 GENE

This following subsection describes the isolation and characterization of a transient receptor protein channel referred to as TRP8. The deduced amino acid sequence of TRP8 shows homology with other TRP proteins. Northern Blot analysis indicates high level expression of TRP8 RNA in taste receptor cells.

6.1. MATERIALS AND METHODS

6.1.1 CLONING OF THE TRP8 GENE

Single cell reverse transcription-polymerase chain reaction (RT-PCR) and differential screening were used to clone genes specifically or selectively expressed in the subset of taste receptor cells that are positive for expression of the G protein gustducin. Individual gustducin-positive cells were isolated from mouse circumvallate papillae (Huang et al. 1999 Nature Neuroscience 2: 1055-1062). The mRNAs from individual cells were reverse transcribed into cDNA followed by PCR amplification. Multiple cDNA libraries from single taste receptor cells were constructed by subcloning the amplified cDNAs into bacteriophage vectors. The cDNA libraries were analyzed by differential screening with self-probe ($P^{32}$-labelled amplified cDNAs from the same cell) and non-self probe ($P^{32}$-labeled amplified cDNAs from another taste cell). Hybridization was carried out at 65° C. for 20 hours in 0.5 M sodium phosphate buffer (pH 7.3) containing 1% bovine serum albumin and 4% SDS. The membranes were washed twice at 65° C. in 0.1% SDS, 0.5×SSC for 20 minutes and one time at 65° C. in 0.1% SDS, 0.1×SSC for 15 minutes. The membranes were exposed to X-ray film at −80° C. with an intensifying screen for three days. Clones which more strongly hybridize to self probe than to non-self probe were isolated and their inserts sequenced.

Using this clone as a probe (LQSEQ91), a mouse taste tissue cDNA library was screened for full-length clones under the same hybridization conditions as specified above. Sequencing the clones containing the longest inserts produced a full-length clone with greatest similarity to a family of calcium channel proteins known as transient receptor potential (TRP) channels.

25 μg of total RNA was isolated by acid guanidinium thiocyanate/phenol/chloroform extraction (P. Chromczynski and N. Sacchi, 1987, Anal. Biochem. 162:156) from the following mouse tissues: taste bud enriched epithelium, nontaste lingual epithelium, brain, retina, olfactory epithelium, stomach, small intestine, liver, spleen, kidney, lung, heart, thymus, uterus, testis and skeletal muscle. The RNAs were electrophoresed on 1.5% agarose gel containing 6.7% formaldehyde, transferred and fixed to a nylon membrane by UV irradiation. The blot was hybridized with a radiolabeled 1.7 kb fragment generated from the 3'-end of mouse TRP 8 cDNA by random priming with Exo(−) Klenow polymerase in the presence of ($\alpha$-$^{32}$P)-dCTP. The hybridization was carried out in 0.25 M sodium phosphate buffer (pH 7.2) containing 7% SDS at 65° C. with agitation for 24 hours.

The membrane was washed twice in 20 mM sodium phosphate buffer (pH 7.2) containing 5% SDS at 65° C. for 40 minutes and twice in the same buffer containing 1% SDS at 65° C. for 40 minutes. The blot was exposed to X-ray film at −80° C. with an intensifying screen for 5 days.

A BLAST search of human high throughput DNA sequences and genomic sequences was done using the mouse TRP8 sequence as the query. From this search a BAC clone was identified that contained the entire human TRP8 gene. The Genscan program was then used to identify the predicted protein-coding exons of the human TRP8 gene. The regions were aligned with the mouse TRP8 cDNA to refine the predicted human TRP8 coding region, leading to deduction of the entire human coding region.

6.1.2. NORTHERN HYBRIDIZATION

Total RNAs were isolated from several mouse tissues using the Trizol reagents, then 25 μg of each RNA was electrophoresed per lane on a 1.5% agarose gel containing 6.7% formaldehyde. The samples were transferred and fixed to a nylon membrane by UV irradiation. The blot was prehybridized at 65° C. in 0.25 M sodium phosphate buffer (pH 7.2) containing 7% SDS and 40 μg/ml herring sperm DNA with agitation for 5 hours; hybridization for 20 hours with the $^{32}$P-radiolabeled mouse TRP8 probe was carried out in the same solution. The membrane was washed twice at 65° C. in 20 mM sodium phosphate buffer (pH 7.2) containing 5% SDS for 40 minutes, twice at 65° C. in the same buffer containing 1% SDS for 40 minutes, and once at 70° C. in 0.1×SSC and 0.1% SDS for 30 minutes. The blot was exposed to X-ray film for 3 days at −80° C. with dual intensifying screens. The $^{32}$P-labeled TRP8 probe was generated by random nonamer priming of a 0.48 kb cDNA fragment of TRP8 corresponding to the 3'-UTR sequence using Exo(−) Klenow polymerase in the presence of ($\alpha$-$^{32}$P)-dCTP.

6.1.3. IN SITU HYBRIDIZATION $^{33}$P-labeled RNA probes [TRP8 (1.7 kb) and α-gustducin (1 kb)] were used for in situ hybridization of frozen sections (10 μm) of mouse lingual tissue. Hybridization and washing were as described (Asano-Miyoshi et al., 2000, *Neurosci Lett* 283:61-4). Slides were coated with Kodak NTB-2 nuclear track emulsion and exposed at 4° C. for 3 weeks and then developed and fixed.

6.1.4. IMMUNOCYTOCHEMISTRY

Polyclonal antisera against a keyhole limpet hemocyanin-conjugated TRP8 peptide (aa 1028-1049) were raised in rabbits. The PLCβ2 antibody was obtained from Santa-Cruz Biotechnologies; the anti-β-gustducin and anti-Gγ13 antibodies were as described (Ruiz-Avila et al., 1995, *Nature* 376:80-5; Huang et al., 1999, *Nat Neurosci* 2:1055-62). Ten micron thick frozen sections of murine lingual tissue (previously fixed in 4% paraformaldehyde and cryoprotected in 20% sucrose) were blocked in 3% BSA, 0.3% Triton X-100, 2% goat serum and 0.1% Na Azide in PBS for 1 hour at room temperature and then incubated for 8 hours at 4° C. with purified antibody against α-gustducin, or antiserum against TRP8 (1:800). The secondary antibodies were Cy3-conjugated goat-anti-rabbit Ig for TRP8 and fluorescein-conjugated goat-anti-rabbit Ig for PLCβ2, α-gustducin or Gγ13. TRP8 immunoreactivy was blocked by preincubation of the antisera with the immunizing peptides at 20 μM. Preimmune serum did not show any immunoreactivity. Sections were double-immunostained with TRP8 plus one of the following antibodies: anti-PLCβ2, anti-α-gustducin or anti-Gγ13. The sections were incubated sequentially with TRP8 antiserum, anti-rabbit-Ig-Cy3 conjugate, normal anti-rabbit-Ig, anti-PLCβ2 (or anti-α-gustducin or anti-Gγ13) antibody and finally with anti-rabbit-Ig-FITC conjugate with intermittent washes between each step. Control sections that were incubated with all of the above except anti-PLCβ2 (or anti-α-gustducin or anti-Gγ13) antibody did not show any fluorescence in the green channel.

6.1.5. GENE EXPRESSION PROFILING

Single taste receptor cell RT-PCR products (5 μl) were fractionated by size on a 1.6% agarose gel and transferred onto a nylon membrane. The expression patterns of the isolated cells were determined by Southern hybridization with 3'-end cDNA probes for mouse TRP8, α-gustducin, Gβ3, Gγ13, PLCβ2 and G3PDH. Blots were exposed for five hours at −80° C. Total RNAs from a single circumvallate papilla and a similar-sized piece of non-gustatory epithelium were also isolated, reverse transcribed, amplified and analyzed as for the individual cells.

6.1.6. HETEROLOGOUS EXPRESSION

Oocytes were injected with 50 ng of TRP8 cRNA. 48 hours after injection oocytes were incubated in Thapsigargin (2 μM) and X-Rhod-1-AM (the $Ca^{++}$ sensing dye) for 3 hours at room temperature.

6.2. RESULTS

6.2.1. IDENTIFICATION OF A NOVEL TRP CHANNEL IN TASTE CELLS

Using single cell reverse transcription-polymerase chain reaction, a clone was isolated that was expressed in gustducin-positive cells but absent from gustducin-negative cells. A search of the expressed sequence tag (EST) dbest database found no matches, suggesting that this clone's pattern of expression is highly restricted to tissues not generally found in EST databases, such as taste tissue.

Using this clone as a probe, a mouse taste tissue cDNA library was screened for full-length clones. Sequencing the clones containing the longest inserts produced a full-length clone with the sequence indicated in FIG. 1. The deduced amino acid sequence of the cDNA clone is shown in FIG. 2.

The isolated cDNA showed the greatest similarity to a family of calcium channel proteins known as transient receptor potential (TRP) channels. The similarity of the isolated clone to this family of proteins indicated that a TRP channel had been identified. Currently seven TRP channels are known to exist, making this clone the eighth member, named by convention TRP8. Mouse TRP8 (TRP8) is most closely related to TRP7 with an identity at the amino acid level of 40%. The predicted topography of the TRP8 channel inserted within the cell membrane is presented in FIGS. 6A-C.

Based upon homology of the mouse clone with a region of human chromosome 11p15.5 contained in a BAC clone (genebank #AC003693) a human TRP8 ortholog was identified. The nucleotide sequence of the human TRP8 gene, as well as the deduced amino acid sequence, are depicted in FIGS. 3A-B (SEQ ID NO: 3) and 4 (SEQ ID NO: 4), respectively. A comparison of the murine and human TRP 8 proteins is shown in FIG. 5 (SEQ ID NO: 2 and SEQ ID NO: 4, respectively). This region of human chromosome 11p15.5 is syntenic with the distal region of mouse chromosome 7. In both cases, TRP8 and hTRP8 map between genes for Kvlqt1 and TSSC4.

6.2.2. TRP8 IS SELECTIVELY EXPRESSED IN TASTE TISSUE

Although TRP8 was identified during a differential screen of α-gustducin-positive (+) vs. α-gustducin (−)⁻ TRCs, it was possible that TRP8 might be more broadly expressed in other taste cells and/or tissues. To determine the tissue distribution of TRP8 mRNA a northern blot with multiple murine tissues was carried out. An TRP8 3'-UTR probe hybridized predominantly to a transcript of 4.5 kb in taste tissue, with no detectable expression in control non-taste tissue. Moderate expression was detected in stomach and small intestine; weak expression was noted in uterus and testis (FIG. 7A). This is in contrast to the results of Enklaar et al., (2000, Genomics 67:179-87). Using an RT-PCR-generated probe designed to amplify the 3' portion of TRP8's coding region they detected highest expression in liver and low level expression in other peripheral tissues (e.g. heart, brain, kidney and testis). Their RT-PCR probe may have detected by cross-hybridization other TRP8 mRNAs or an alternatively spliced MRNA with a different 3'-end from that present in our 3'-UTR probe. As an independent measure of expression of TRP8, we carried out western blots using an anti-TRP8 antibody (FIG. 7B). TRP8 protein of the predicted molecular weight (~130 kDa) was detected in stomach and small intestine; a species of higher than expected molecular weight was identified in liver and kidney and may represent either an TRP8 -related protein or an TRP8 product from an alternatively spliced message.

6.2.3. TRP8 IS EXPRESSED IN PARTICULAR SUBSETS OF TASTE RECEPTOR CELLS

In situ hybridization was used to determine the cellular pattern of expression of TRP8 in mouse TRCs. TRP8 mRNA was observed in TRCs in circumvallate and foliate papillae, but not in the surrounding non-gustatory epithelia (FIG. 8). TRP8⁺ TRCs were present in the majority of the taste buds, although not all TRCs were positive, suggesting restricted expression to a subset of TRCs. The general pattern of TRP8 expression was comparable to that of α-gustducin, although the α-gustducin signal was somewhat more intense (FIG. 8D). Controls with sense probes showed minimal non-specific hybridization to taste tissue with either the TRP8 probe (FIG. 8B) or the (α-gustducin probe (FIG. 8E).

To determine if TRP8 is co-expressed in TRCs with signal transduction elements that might be involved in its activation, we performed single and double immunohistochemistry of TRC-containing tissue sections. TRP8 protein was co-expressed absolutely with Gγ13 (FIG. 9ABC) and PLCβ2 (FIG. 9GHI), suggesting that these three molecules might be part of a common signal transduction pathway. TRP8 co-expressed largely, but not absolutely, with (α-gustducin (FIG. 9DEF): a subset of the TRP8⁺ TRCs were negative for α-gustducin, although all α-gus⁺ TRCs were positive for TRP8. This pattern is consistent with our observations that α-gus⁺ TRCs constitute a subset of TRCs that are positive for Gγ13, Gβ1, PLCβ2 and IP₃R3 (Huang et al, 1999,). The slight differences in distribution at the cellular level among the different molecules could be explained by the different topologies that each protein displays: TRP8 is an integral membrane protein, whereas α-gustducin and PLCβ2 are membrane-associated proteins. The expression of human TRP8 (hTRP8 ) in human fungiform taste buds was also confirmed.

To independently monitor co-expression of TRP8 in TRCs with the above-mentioned signal transduction elements, as well as with Gβ1 and Gβ3, a single cell expression profiling was carried out (Huang et al., 1999, Nat Neurosci 2:1055-62)). In this way it was determined that expression of α-gustducin, Gβ1, Gβ3, Gγ13, PLCβ2 and TRP8 was restricted to taste tissue (FIG. 10, left panel), and that in this set of 24 TRCs, TRP8 co-expressed absolutely with α-gustducin, Gβ3, Gγ13, PLCβ2 (FIG. 10, right panel); expression of TRP8 also overlapped in large part with that of Gβ1 (15 of 19 TRP8⁺ cells were also Gβ1⁺). The coincident expression of these various signal transduction molecules with TRP8 could provide the physical opportunity for activation of TRP8 by IP₃ (by activation of IP₃ receptors) or DAG (by direct activation of TRP8) generated by a signaling pathway in which GPCRs coupled to heterotrimeric gustducin (i.e. α-gustducin/β3/γ13) or to other Gα/β1,β3/γ13-containing heterotrimers might release βγ to activate PLCβ2. Consistent with this is the recent identification in TRCs of IP₃ receptor subtype III (IP₃R3), and the demonstration that IP₃R3 co-localizes in large part with α-gustducin, Gγ13 and PLCβ2.

6.2.4. OTHER TRP FAMILY MEMBERS ARE NOT DETECTABLY EXPRESSED IN TASTE TISSUE

Native TRP channels are thought to form homo- and hetero-multimers. To identify potential partners for TRP8 in TRCs PCR was used to determine if murine TRP channels 1-6 (TRP 1-6) are expressed in taste tissue (brain tissue provided a positive control). Amplification by the PCR using primer pairs specific for TRP 1-6 identified products of the correct size for all six TRP family members when brain cDNA was used as the template (FIG. 11, lower panel); DNA sequencing of these products confirmed amplification of all six TRP family members. TRP8 was not amplified when brain cDNA was the template (FIG. 11, lower panel), although it was amplified when taste cDNA provided the template (FIG. 11, upper panel) (amplification of TRP8 was confirmed by DNA sequencing). None of the other six TRP family members were amplified when taste tissue cDNA was used as the template (FIG. 11, upper panel), suggesting that they are not highly expressed, if at all, in TRCs. In a separate experiment using TRP7 specific primers, TRP7 was detected by PCr in brain cDNA, but not in taste cDNA. Novel TRP channels beyond these seven members might be expressed in TRCs, but at the present time it would appear that TRP8 is the only known TRP channel highly expressed in taste tissue, and as shown above, in TRCs.

6.2.5. EXPRESSED TRP8 ACTS AS A STORE OPERATED CHANNEL

To determine if TRP8 can function as a calcium channel, TRP8 was expressed in Xenopus oocytes. The oocytes possess an endogenous calcium-activated chloride conductance (ICl$_{Ca}$) that may be used to monitor Ca⁺⁺ influx due to activation of store operated Ca⁺⁺ channels belonging to the TRP family. TRP8 RNA obtained by in vitro transcription was injected into Xenopus oocytes and two electrode voltage clamp recordings were performed two days later. To induce depletion of internal Ca⁺⁺ stores, oocytes were incubated for 2 hours before the recording in 2 μM thapsigargin (TPN), an irreversible inhibitor of the sarco(endo)plasmic reticulum $Ca^{++}$-ATPase (SERCA).

Representative recording traces of oocytes injected with TRP8 RNA and treated with TPN demonstrated a robust and distinct inward current elicited by the addition of $Ca^{++}$ to the external bath (FIG. 12A). These traces differ dramatically from those of control oocytes injected with water (FIG. 12B), indicating that TRP8 encodes a functional $Ca^{++}$ channel whose activation is dependent on the filling status of the internal $Ca^{++}$ stores (compare FIG. 12 panels A and B), and whose function relies on the availability of external $Ca^{++}$. The control oocytes express an endogenous TRP channel (XTrp) (Bobanovic et al., 1999, *Biochem J.* 340:593-9)) that can be activated by TPN treatment (FIG. 12B). Analysis of the total inward current (FIG. 12D) generated under conditions when $Ca^{++}$ is present in the extracellular medium clearly demonstrated the effect of TRP8 expression. To confirm that TRP8 protein was actually expressed in the oocytes, we carried out a western blot of the membrane proteins from TRP8 RNA-injected oocytes using an anti-TRP8 antibody: a 130 kDa protein of the expected size was detected.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Various references are cited herein, the disclosures of which are incorporated by reference in their entireties.

We claim:

1. A method for identifying a compound that potentially induces the perception of a bitter taste comprising:
   (i) contacting an isolated cell expressing the TRP8 channel protein of SEQ ID NO: 4 with a test compound and measuring the level of TRP8 activation;
   (ii) in a separate experiment, contacting an isolated cell expressing the TRP8 channel protein of SEQ ID NO: 4 with a vehicle control and measuring the level of TRP8 activation where the conditions are essentially the same as in part (i); and
   (iii) comparing the level of activation of TRP8 measured in part (i) with the level of activation of TRP8 in part (ii),
   wherein the level of TRP8 activation is measured by measuring the membrane potential of the cell and wherein an increased level of activated TRP8 in the presence of the test compound indicates that the test compound potentially induces the perception of a bitter taste.

2. The method according to claim 1, wherein said measuring the level of TRP8 activation is carried out with one or more fluorescence-indicator dyes.

3. The method according to claim 1, wherein said measuring the membrane potential of the cell is carried out under voltage clamp assay conditions.

4. The method according to claim 1, wherein said measuring the membrane potential of the cell is carried out under patch recording assay conditions.

* * * * *

UNITED STATES PATENT AND TRADEMARK OFFICE
CERTIFICATE OF CORRECTION

| | |
|---|---|
| PATENT NO. | : 7,364,867 B2 |
| APPLICATION NO. | : 09/834792 |
| DATED | : April 29, 2008 |
| INVENTOR(S) | : Margolskee et al. |

It is certified that error appears in the above-identified patent and that said Letters Patent is hereby corrected as shown below:

Col. 1 at line 9, insert --This invention was made with government support under grant numbers 0255-5411, 0255-4341, and 0254-8321 awarded by the National Institutes of Health. The government has certain rights in this invention.--.

Signed and Sealed this

Eighth Day of December, 2009

David J. Kappos
*Director of the United States Patent and Trademark Office*